(12) United States Patent
Sannino et al.

(10) Patent No.: US 11,130,823 B2
(45) Date of Patent: *Sep. 28, 2021

(54) METHOD FOR PRODUCING HYDROGELS

(71) Applicant: Gelesis LLC, Boston, MA (US)

(72) Inventors: Alessandro Sannino, Lecce (IT); Christian Demitri, San Pietro in Lama (IT); Yishai Zohar, Brookline, MA (US); Barry Joseph Hand, Acton, MA (US); Eyal S. Ron, Lexington, MA (US)

(73) Assignee: Gelesis LLC, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/773,164

(22) Filed: Jan. 27, 2020

(65) Prior Publication Data

US 2020/0332025 A1 Oct. 22, 2020

Related U.S. Application Data

(60) Continuation of application No. 15/139,896, filed on Apr. 27, 2016, now Pat. No. 10,544,233, which is a
(Continued)

(51) Int. Cl.
*C08B 11/12* (2006.01)
*C08L 1/28* (2006.01)
(Continued)

(52) U.S. Cl.
CPC ............... *C08B 3/12* (2013.01); *A23L 33/24* (2016.08); *A61K 31/738* (2013.01); *A61P 3/04* (2018.01);
(Continued)

(58) Field of Classification Search
None
See application file for complete search history.

(56) References Cited

U.S. PATENT DOCUMENTS

| 3,526,048 A | 9/1970 | Rowland et al. |
| 4,609,640 A | 9/1986 | Morishita et al. |

(Continued)

FOREIGN PATENT DOCUMENTS

| CA | 2812246 A1 | 10/2013 |
| DE | 212969 | 8/1984 |

(Continued)

OTHER PUBLICATIONS

"MP Biomedicals Technical Information for Carboxymethyl cellulose Sodium Salt" 2010.
(Continued)

*Primary Examiner* — Eric Olson
(74) *Attorney, Agent, or Firm* — Elmore Patent Law Group, P.C.; Carolyn S. Elmore; Edgar W. Harlan

(57) ABSTRACT

The present invention provides a method of producing a polymer hydrogel comprising the steps of: (1) preparing an aqueous solution of a water soluble polysaccharide derivative and a polycarboxylic acid; (2) optionally agitating the solution, for example, by stirring; (3) isolating a polysaccharide derivative/polycarboxylic acid composite from the solution; and (4) heating the polysaccharide derivative/polycarboxylic acid composite at a temperature of at least about 80° C., thereby cross-linking the polysaccharide with the polycarboxylic acid. The invention also provides polymer hydrogels produced by the methods of the invention.

14 Claims, 11 Drawing Sheets

US 11,130,823 B2

Page 2

Related U.S. Application Data division of application No. 13/491,197, filed on Jun. 7, 2012, now Pat. No. 9,353,191.

(60) Provisional application No. 61/494,298, filed on Jun. 7, 2011, provisional application No. 61/542,494, filed on Oct. 3, 2011.

(51) Int. Cl.
| | |
|---|---|
| C08B 15/00 | (2006.01) |
| A61P 3/04 | (2006.01) |
| A23L 33/24 | (2016.01) |
| A61K 31/738 | (2006.01) |
| C08B 3/12 | (2006.01) |
| C08B 11/08 | (2006.01) |
| C08B 11/20 | (2006.01) |
| C08L 1/08 | (2006.01) |
| C08J 3/075 | (2006.01) |

(52) U.S. Cl.
CPC .............. *C08B 11/08* (2013.01); *C08B 11/12* (2013.01); *C08B 11/20* (2013.01); *C08B 15/005* (2013.01); *C08J 3/075* (2013.01); *C08L 1/08* (2013.01); *C08L 1/284* (2013.01); *C08L 1/286* (2013.01); *C08J 2301/00* (2013.01); *C08J 2301/08* (2013.01); *C08J 2301/26* (2013.01); *C08J 2301/28* (2013.01); *Y10T 428/2982* (2015.01)

(56) References Cited

U.S. PATENT DOCUMENTS

| | | | |
|---|---|---|---|
| 4,697,008 | A | 9/1987 | Asano et al. |
| 5,047,513 | A | 9/1991 | Doebeli et al. |
| 5,137,537 | A | 8/1992 | Herron et al. |
| 5,247,072 | A | 9/1993 | Ning et al. |
| 5,415,864 | A | 5/1995 | Kopecek et al. |
| 5,550,189 | A | 8/1996 | Qin et al. |
| 5,676,964 | A | 10/1997 | Della et al. |
| 5,736,595 | A | 4/1998 | Guenther et al. |
| 5,800,418 | A | 9/1998 | Ahr |
| 5,847,031 | A | 12/1998 | Klimmek et al. |
| 5,873,979 | A | 2/1999 | Naieni et al. |
| 6,271,278 | B1 | 8/2001 | Park et al. |
| 6,436,441 | B1 | 8/2002 | Sako et al. |
| 6,471,824 | B1 | 10/2002 | Jewell et al. |
| 6,630,422 | B1 | 10/2003 | Sannino et al. |
| 6,686,464 | B1 | 2/2004 | Harding et al. |
| 6,765,042 | B1 | 7/2004 | Besemer et al. |
| 7,071,327 | B2 | 7/2006 | Mensitieri et al. |
| 7,300,965 | B2 | 11/2007 | Weerawarna et al. |
| 8,658,147 | B2 | 2/2014 | Nicolais et al. |
| 9,353,191 | B2 | 5/2016 | Sannino et al. |
| 9,855,294 | B2 | 1/2018 | Heshmati et al. |
| 10,098,907 | B2 | 10/2018 | Sannino et al. |
| 10,179,824 | B2 | 1/2019 | Sannino et al. |
| 10,584,183 | B2 * | 3/2020 | Sannino .................... A61P 3/10 |
| 2001/0002411 | A1 | 5/2001 | Ronan et al. |
| 2001/0006677 | A1 | 7/2001 | McGinity et al. |
| 2003/0144642 | A1 | 7/2003 | Dopps et al. |
| 2003/0232895 | A1 | 12/2003 | Omidian et al. |
| 2004/0157734 | A1 | 8/2004 | Mertens et al. |
| 2004/0236016 | A1 | 11/2004 | Thornton et al. |
| 2005/0031680 | A1 | 2/2005 | Simon et al. |
| 2005/0100603 | A1 | 5/2005 | Sako et al. |
| 2005/0118326 | A1 | 6/2005 | Anfinsen et al. |
| 2005/0143571 | A1 | 6/2005 | Stoyanov et al. |
| 2006/0102483 | A1 | 5/2006 | Chuang et al. |
| 2006/0142478 | A1 | 6/2006 | Luo et al. |
| 2006/0142480 | A1 | 6/2006 | Luo et al. |
| 2006/0286264 | A1 | 12/2006 | Don et al. |
| 2007/0231366 | A1 | 10/2007 | Sawhney et al. |
| 2008/0009616 | A1 | 1/2008 | Frank et al. |
| 2008/0070997 | A1 | 3/2008 | Takigami et al. |
| 2008/0095911 | A1 | 4/2008 | Adams et al. |
| 2008/0103228 | A1 | 5/2008 | Falcone et al. |
| 2008/0147026 | A1 | 6/2008 | Qin et al. |
| 2008/0166410 | A1 | 7/2008 | Funk et al. |
| 2008/0227944 | A1 | 9/2008 | Ambrosio et al. |
| 2008/0241094 | A1 | 10/2008 | Burnett et al. |
| 2008/0262155 | A1 | 10/2008 | Mertens et al. |
| 2009/0099541 | A1 | 4/2009 | Qin et al. |
| 2009/0311235 | A1 | 12/2009 | Elenko et al. |
| 2009/0324537 | A1 | 12/2009 | Bucevschi et al. |
| 2010/0234233 | A1 | 9/2010 | Sannino et al. |
| 2012/0052151 | A1 | 3/2012 | Sannino et al. |
| 2013/0089737 | A1 | 4/2013 | Sannino et al. |
| 2013/0195975 | A1 | 8/2013 | Simon et al. |
| 2014/0296507 | A1 | 10/2014 | Sannino et al. |
| 2015/0366898 | A1 | 12/2015 | Ron et al. |
| 2018/0153925 | A1 | 6/2018 | Heshmati et al. |
| 2020/0277407 | A1 * | 9/2020 | Sannino ............... A61K 31/738 |

FOREIGN PATENT DOCUMENTS

| | | |
|---|---|---|
| DE | 212969 A1 | 8/1984 |
| DE | 19654745 A1 | 7/1998 |
| EP | 0637594 A2 | 8/1994 |
| JP | H0782301 A | 3/1995 |
| JP | 2004010634 A | 1/2004 |
| JP | 2008069315 A | 3/2008 |
| JP | 2008195649 A | 8/2008 |
| JP | 2008285611 A | 11/2008 |
| WO | 9602276 A2 | 2/1996 |
| WO | 9926670 A1 | 6/1999 |
| WO | 0032064 A1 | 6/2000 |
| WO | 2006056079 A1 | 6/2006 |
| WO | 2006070337 A2 | 7/2006 |
| WO | 2007112436 A2 | 10/2007 |
| WO | 2007115169 A2 | 10/2007 |
| WO | 2009021701 A2 | 2/2009 |
| WO | 2009022358 A1 | 2/2009 |
| WO | 2010059725 A1 | 5/2010 |
| WO | 2014074696 A1 | 5/2014 |

OTHER PUBLICATIONS

"Prevention", in Glossary of medical education terms: Parts 1-7. Wojtczak, A., Ed. Medical Teacher. vol. 24, Nos. 2-6 and vol. 25, No. 1 & 2, 2002.
Walocel™ C USP/EP Carboxymethyl Cellulose Sodium for Pharmaceutical Applications-Dow Chemical (2014).
Anbergen, et al., "Elasticity and swelling behaviour of chemically crosslinked cellulose ethers in aqueous systems", Polymer, 31, 1990, 1854-1858.
Capitani, et al., "13C Solid-State NMR Determination of Cross-Linking Degree in Superabsorbing Cellulose-Based Networks", Macromolecules, 33, 2000, 430-437.
Casciaro, et al., "Experimental investigation and theoretical modelling of the nonlinear acoustical behaviour of a liver tissue and comparison with a tissue mimicking hydrogel", J. Mater Sci: Mater Med, 19, 2008, 899-906.
Casciaro, et al., "Full experimental modelling of a liver tissue mimicking phantom for medical ultrasound studies employing different hydrogels", J. Mater Sci: Mater Med, 20, 2009, 983-989.
Chang, et al., "Structure and properties of hydrogels prepared from cellulose in NaOH/urea aqueous solutions", Carbohydrate Polymers, 82, 2010, 122-127.
Chang, et al., "Superabsorbent hydrogels and based on cellulose for smart swelling and controllable delivery", European Polymer Journal, 46, 2010, 92-100.
Coma, et al., "Film properties from crosslinking of cellulosic derivatives with a polyfunctional carboxylic acid", Carbohydrate Polymers, 51, 2003, 265-271.
Demitri, et al., "Hydrogel Based Tissue Mimicking Phantom for In-Vitro Ultrasound Contrast Agents Studies", J. Biomed Mater Res Part B: Appl Biomater, 87B, 2008, 338-345.

(56) References Cited

OTHER PUBLICATIONS

Demitri, C. et al., "Novel Superabsorbent Cellulose-Based Hydrogels Crosslinked with Citric Acid", Journal of Applied Polymer Science, 110(4), Aug. 20, 2008, 2453-2460.

Esposito, et al., "Response of intestinal cells and macrophages to an orally administered cellulose-PEG based polymer as a potential treatment for intractable edemas", Biomaterials, 26, 2005, 4101-4110.

Esposito, F. et al., "Water Sorption in Cellulose-Based Hydrogels", Journal of Applied Polymer Science, 60, 1996, 2403-2407.

Gorgieva, et al., "Synthesis and application of new temperature-responsive hydrogels based on carboxymethyl and hydroxyethyl cellulose derivatives for the functional finishing of cotton knitwear", Carbohydrate Polymers, 85, 2011, 664-673.

Hashem, et al., "Synthesis and characterization of novel carboxymethylcellulose hydrogels and carboxymethylcellulose-hydrogel-ZnO-nanocomposites", Carbohydrate Polymers, 95(1), 2013, 421-427.

Hoogendam, C. W. et al., "Persistence length of carboxymethyl cellulose as evaluated from size exclusion chromatography and potentionmetric titrations", Macromolecules, 31, 1998, 6297-6309.

Ito, "The prevention of peritoneal adhesions by in situ cross-linking hydrogels of hyaluronic acid and cellulose derivatives", Biomaterials, 28:, 2007, 975-983.

Kadajji, V G. et al., "Water Soluble Polymers for Pharmaceutical Applications", Polymers 3, 2011, 1972-2009.

Kose, G. T. et al., "Macroporous poly(3-hydroxybutyrate-co-3-hydroxyvalerate) matrices for bone tissue engineering", Biomaterials, 24, 2003, 1949-1958.

Lenzi, et al., "Probing the degree of crosslinking of a cellulose based superabsorbing hydrogel through traditional and NMR techniques", Polymer, 44:, 2003, 1577-1588.

Lionetto, et al., "Ultrasonic monitoring of the network formation in superabsorbent cellulose based hydrogels", Polymer, 46, 2005, 1796-1803.

Liu, et al., "Radiation crosslinking of CMC-Na at low dose and its application as substitute for hydrogel", Radiation Physics and Chemistry, 72:, 2005, 635-638.

Liu, et al., "Radiation preparation and swelling behavior of sodium carboxymethyl cellulose hydrogels", Radiation Physics and Chemistry, 63, 2002, 525-528.

Marci, et al., "Environmentally sustainable production of cellulose-based superabsorbent hydrogels", Green Chem., 8, 2006, 439-444.

Qiu, et al., "Effect of activated carbon on the properties of carboxymethylcellulose/activated carbon hybrid hydrogels synthesized by γ-radiation techniqu", Carbohydrate Polymers, 70:, 2007, 236-242.

Raucci, M. G. et al., "Effect of citric acid crosslinking cellulose-based hydrogels on osteogenic differentiation", Journal of Biomedical Materials Research, 103(6), 2014, 2045-2056.

Sannino, et al., "A Cellulose-Based Hydrogel as a Potential Bulking Agent for Hypocaloric Diets: An In Vitro Biocompatibility Study on Rat Intestine", Journal of Applied Polymer Science, 102, Jul. 28, 2006, 1524-1530.

Sannino, et al., "Biodegradable-Cellulose-based Hydrogels: Design and Applications", Materials, 2:, 2009, 353-373.

Sannino, et al., "Biomedical application of a superabsorbent hydrogel for body water elimination in the treatment of edemas", J. Biomed. Mater Res., 67A, 2003, 1016-1024.

Sannino, et al., "Cellulose Derivative-Hyaluronic Acid-Based Microporous Hydrogels Cross-Linked through Divinyl Sulfone (DVS) to Modulate Equilibrium Sorption Capacity and Network Stability", Biomacromolecules, 5, 2004, 92-96.

Sannino, et al., "Cellulose-based hydrogels as body water retainers", J. Mater Sci: Mat in Med., 11, 2000, 247-253.

Sannino, et al., "Concurrent effect of microporosity and chemical structure on the equilibrium sorption properties of cellulose-based hydrogels", Polymer, 46, 2005, 4676-4685.

Sannino, et al., "Crosslinking of cellulose derivatives and hyaluronic acid with water-soluble carbodiimide", Polymer, 46, 2005, 11206-11212.

Sannino, et al., "Designing microporous macromolecular hydrogels for biomedical applications: a comparison between two techniques", Composites Science and Technology, 63, 2003, 2411-2416.

Sannino, et al., "Development and Characterization of Cellulose-Based Hydrogels for Use as Dietary Bulking Agents", Journal of Applied Polymer Science, 115, 2010, 1438-1444.

Sannino, et al., "Introduction of Molecular Spacers Between the Crosslinks of a Cellulose-Based Superabsorbent Hydrogel: Effects on the Equilibrium Sorption Properties", Journal of Applied Polymer Science, 90, 2003, 168-174.

Sannino, et al., "Spin Coating Cellulose Derivatives on Quartz Crystal Microbalance Plates to Obtain Hydrogel- Based Fast Sensors and Actuators", Journal of Applied Polymer Sci., 106, 2007, 3040-3050.

Sannino, et al., "Water and Synthetic Urine Sorption Capacity of Cellulose-Based Hydrogels under a Compressive Stress Field", Journal of Applied Polymer Science, 91, 2004, 3791-3796.

Srokova, I et al., "Water-Soluble Amphiphilic 0-(Carboxymethyl)-cellulose Derivatieves—Synthesis and Properties", Macromolecular Materials Engineering 289, 2004, 63-69.

Xie, et al., "Development and Physicochemical Characterization of New Resistant Citrate Starch from Different Corn Starches", Starch, 56, 2004, 364-270.

Ogushi, et al., "Synthesis of Enzymatically-Gellable Carboxymethylcellulose for Biomedical Applications", Journal of Bioscience and Bioengineering, 104(1):, 2007, 30-33.

* cited by examiner

METHOD FOR PRODUCING HYDROGELS

RELATED APPLICATIONS

This application is a continuation of U.S. application Ser. No. 15/139,896, filed on Apr. 27, 2016, which is a divisional of U.S. application Ser. No. 13/491,197, filed on Jun. 7, 2012 (now U.S. Pat. No. 9,353,191), which claims the benefit of U.S. Provisional Application No. 61/494,298, filed on Jun. 7, 2011 and U.S. Provisional Application No. 61/542,494, filed on Oct. 3, 2011. The entire teachings of the above applications are incorporated herein by reference.

BACKGROUND OF THE INVENTION

Polymer hydrogels are cross-linked hydrophilic polymers which are capable of absorbing and retaining large amounts of water. Certain of these materials are capable of absorbing over 1 Kg of water per gram of dry polymer. The cross-links between the macromolecular chains form a network which guarantees the structural integrity of the polymer-liquid system and prevents the complete solubilisation of the polymer while allowing the retention of the aqueous phase within the molecular mesh. Polymer hydrogels having a particularly large capacity to retain water are referred to as superabsorbent polymer hydrogels (SAPs). High absorbency under load (AUL) is also a common characteristic of SAPs which is in general is not displayed by polymer hydrogels having lower capacity to retain water. In addition to pressure, pH and other environmental conditions can affect the water retainment capacity of a polymer hydrogel, such as a SAP. Applications of highly absorbent polymer hydrogels include as absorbent cores in the field of absorbent personal hygiene products (Masuda, F., *Superabsorbent Polymers*, Ed. Japan Polymer Society, Kyoritsu Shuppann, (1987)) and as devices for the controlled release of water and nutrients into arid soils.

Carboxyalkyl cellulose materials and other carboxyalkyl polysaccharides are known in the art. Carboxyalkyl cellulose materials can be formed by treating a cellulosic material with a carboxyalkylating agent, such as a chloroalkanoic acid, usually monochloroacetic acid, and an alkali, such as sodium hydroxide, optionally in the presence of an alcohol. Such carboxyalkyl celluloses are generally water-soluble. Various methods of rendering such water-soluble carboxyalkyl celluloses water-insoluble are known. However, these methods rely on a stabilization mechanism which does not include the use of any cross-linker; the procedure involves selecting a proper range of temperature and heat treating time to transform the water soluble cellulose derivative into a non-water soluble form. The resulting stabilization appears to be mainly due to physical rather than chemical effects. In fact, at certain pH values, generally from about pH 10 and higher, the cellulose derivatives become water soluble again. [Flory, J. P. Principles of Polymer Chemistry; Cornell University: Ithaca, N.Y., 1953].

Other methods for the insolubilization of carboxyalkyl cellulose materials include the heat treatment of the carboxyalkyl cellulose in the presence of excess carboxyalkylating reactants and by-products of the carboxyalkylation reaction, to provide a water-insoluble carboxyalkyl cellulose having desirable liquid absorption and retention properties and characteristics. In these cases, the use of accelerators and catalysts to promote the stabilization (i.e., permanent cross-linking), coupled to a non uniform distribution of the degree of cross-linking, result in an insoluble material having a low swelling capacity (Anbergen U., W. Opperman, Polymer, 31, 1854 (1990), Nijenhuis, K.te, *Advances in Polymer Science*, 130, (1997)).

Cellulose-based hydrogels can be obtained via either physical or chemical stabilization of aqueous solutions of cellulosics. Additional natural and/or synthetic polymers have been combined with cellulose to obtain composite hydrogels with specific properties [Chen, H.; Fan, M. Novel thermally sensitive pH-dependent chitosan/carboxymethylcellulose hydrogels. J. Bioact. Compat. Polym. 2008, 23 (1), 38-48. Chang, C.; Lue, A.; Zhang, L. Effects of cross-linking methods on structure and properties of cellulose/PVA hydrogels. Macromol. Chem. Phys., 2008, 209 (12), 1266-1273] (A. Sannino, M. Madaghiele, F. Conversano, A. Maffezzoli, P. A. Netti, L. Ambrosio and L. Nicolais' "Cellulose derivative-hyaluronic acid based microporous hydrogel cross-linked through divinyl sulfone (DVS) to modulate equilibrium sorption capacity and network stability", *Biomacromolecules*, Vol. 5, no 1 (2004) 92-96). Physical, thermoreversible gels are usually prepared from water solutions of methylcellulose and/or hydroxypropyl methylcellulose (in a concentration of 1-10% by weight) [Sarkar, N. Thermal gelation properties of methyl and hydroxypropyl methylcellulose. J. Appl. Polym. Sci., 1979, 24 (4), 1073-1087]. The gelation mechanism involves hydrophobic associations among the macromolecules possessing the methoxy group. At low temperatures, polymer chains in solution are hydrated and simply entangled with one another. As temperature increases, macromolecules gradually lose their water of hydration, until polymer-polymer hydrophobic associations take place, thus forming the hydrogel network. The sol-gel transition temperature depends on the degree of substitution of the cellulose ethers as well as on the addition of salts. A higher degree of substitution of the cellulose derivatives provides them a more hydrophobic character, thus lowering the transition temperature at which hydrophobic associations take place. A similar effect is obtained by adding salts to the polymer solution, since salts reduce the hydration level of macromolecules by recalling the presence of water molecules around themselves. Both the degree of substitution and the salt concentration can be properly adjusted to obtain specific formulations gelling at 37° C. and thus potentially useful for biomedical applications [Tate, M. C.; Shear, D. A.; Hoffman, S. W.; Stein, D. G.; LaPlaca, M. C. Biocompatibility of methylcellulose-based constructs designed for intracerebral gelation following experimental traumatic brain injury. Biomaterials, 2001, 22 (10), 1113-1123. Materials, 2009, 2, 370 Chen, C.; Tsai, C.; Chen, W.; Mi, F.; Liang, H.; Chen, S.; Sung, H. Novel living cell sheet harvest system composed of thermoreversible methylcellulose hydrogels. Biomacromolecules, 2006e7 (3), 736-743. Stabenfeldt, S. E.; Garcia, A. J.; LaPlaca, M. C. Thermoreversible laminin-functionalized hydrogel for neural tissue engineering. J. Biomed. Mater. Res., A 2006, 77 (4), 718-725.]. However, physically cross-linked hydrogels are reversible [Te Nijenhuis, K. On the nature of cross-links in thermoreversible gels. Polym. Bull., 2007, 58 (1), 27-42], and thus might flow under given conditions (e.g., mechanical loading) and might degrade in an uncontrollable manner. Due to such drawbacks, physical hydrogels based on methylcellulose and hydroxypropylmethylcellulose (HPMC) are not recommended for use in vivo.

As opposed to physical hydrogels which show flow properties, stable and stiff networks of cellulose can be prepared by inducing the formation of chemical, irreversible cross-links among the cellulose chains. Either chemical agents or physical treatments (i.e., high-energy radiation) can be used to form stable cellulose-based networks. The degree of cross-linking, defined as the number of cross-linking sites per unit volume of the polymer network, affects the diffusive, mechanical and degradation properties of the hydrogel, in addition to the sorption thermodynamics, and can be controlled to a certain extent during the synthesis. Specific chemical modifications of the cellulose backbone might be performed before cross-linking, in order to obtain stable hydrogels with given properties. For instance, silylated HPMC has been developed which cross-links through condensation reactions upon a decrease of the pH in water solutions.

As a further example, tyramine-modified sodium carboxymethylcellulose (NaCMC) has been synthesized to obtain enzymatically gellable formulations for cell delivery [Ogushi, Y.; Sakai, S.; Kawakami, K. Synthesis of enzymatically-gellable carboxymethylcellulose for biomedical applications. J. Biosci. Bioeng., 2007, 104 (1), 30-33]. Photocross-linking of aqueous solutions of cellulose derivatives is achievable following proper functionalization of cellulose. However, the use of chemical cross-linker and/or functionalizing agents provides a product which is not suitable for oral administration, especially in significant amounts and chronic use.

SUMMARY OF THE INVENTION

The present invention relates to the discovery that cross-linking water-soluble cellulose derivatives, such as carboxymethylcellulose, with low levels of a polycarboxylic acid, such as citric acid (3-carboxy-3-hydroxy-1,5-pentanedioic acid); hereinafter also designated "CA") results in the formation of highly absorbent polymer hydrogels having significant water absorption properties, mechanical stability and other advantageous characteristics.

The present invention relates, in addition, to improved processes for producing polymer hydrogels, including superabsorbent polymer hydrogels, by cross-linking a soluble polysaccharide derivative, such as a carboxyalkyl polysaccharide, a hydroxyalkyl polysaccharide or a combination thereof, with a polycarboxylic acid. The invention further relates to the polymer hydrogels produced using these processes and polymer hydrogels having advantageous properties.

In one embodiment, the invention provides a method of producing a polymer hydrogel comprising the steps of (1) preparing an aqueous solution of a water soluble polysaccharide derivative and a polycarboxylic acid; (2) optionally agitating the solution, for example, by stirring; (3) isolating a polysaccharide derivative/polycarboxylic acid composite from the solution and (4) heating the polysaccharide derivative/polycarboxylic acid composite at a temperature of at least about 80° C., thereby cross-linking the polysaccharide with the polycarboxylic acid. In one embodiment, the polysaccharide derivative/polycarboxylic acid composite is granulated prior to conducting step (4). In one embodiment, the polysaccharide derivative/polycarboxylic acid composite is heated in step (4) to a temperature of about 100° C. or higher.

The aqueous solution of polysaccharide derivative and polycarboxylic acid is preferably prepared by adding the polysaccharide derivative and the polycarboxylic acid to water and agitating, for example by stirring, the resulting mixture for a sufficient amount of time to create a homogenous solution.

The polysaccharide derivative is preferably present in the solution of step (1) in a concentration of at least about 0.25% by weight relative to water, preferably at least about 0.4% or 0.5%. In one embodiment, the concentration of the polysaccharide derivative is from about 0.25% to about 25% or about 0.25% to about 30%, by weight relative to water, preferably from about 0.4% to about 20% and more preferably from about 0.4% to about 12%. In certain embodiments, the polysaccharide derivative is present in the solution at a concentration of at least about 4%, for example from about 4% to about 30%, about 4% to about 20%, about 4% to about 10% by weight relative to water. In one embodiment, the polysaccharide derivative is present in the solution of step (1) at a concentration of about 6% by weight relative to water. In certain embodiments, the polysaccharide concentration is from about 4% to about 8%, from about 4.5% to about 7.5%, from about 5% to about 7%, or from about 5.5% to about 6.5% by weight relative to water. In other embodiments, the polysaccharide concentration is 0.25% to about 6%, about 0.4% to about 6% or about 0.5% to about 6% by weight relative to water. In one embodiment, the concentration of the polysaccharide derivative is from about 0.5% to about 1%, 1.5% or 2% by weight relative to water. In one embodiment, the solution includes undissolved polysaccharide derivative, that is, the amount of polysaccharide derivative exceeds its solubility and a suspension or slurry is formed.

The polycarboxylic acid is preferably present in the solution of step (1) in a concentration of about 0.01% to about 5% or about 0.05 to about 5% by weight relative to the polysaccharide derivative. Preferably, the polycarboxylic acid is present in a concentration of about 0.3% or less or 0.35% or less by weight relative to the polysaccharide derivative. In an embodiment, the polycarboxylic acid is present in the solution of step (1) in a concentration of about 0.01% to about 0.35%, about 0.05% to about 0.35%, about 0.1% to about 0.35%, 0.01% to about 0.3%, about 0.05% to about 0.3%, about 0.1% to about 0.3%, 0.15% to about 0.35%, about 0.15% to about 0.3%, 0.2% to about 0.35%, about 0.25% to about 0.35%, about 0.2% to about 0.3%, or about 0.25% to about 0.3%, by weight relative to the polysaccharide derivative.

In another embodiment, the polycarboxylic acid is preferably present in the solution of step (1) in a concentration of about 0.05 to about 5% (g/g) relative to the monomeric units of the polysaccharide derivative. Preferably, the polycarboxylic acid is present in a concentration of about 0.35% (g/g) or 0.3% or less relative to the monomeric units of the polysaccharide derivative. In an embodiment, the polycarboxylic acid is present in the solution of step (1) in a concentration of about 0.05% to about 0.3%, about 0.1% to about 0.3%, 0.2% to about 0.3% or about 0.25% to about 0.3% (g/g) relative to the monomeric units of the polysaccharide derivative.

In one embodiment, the aqueous solution consists essentially of the polysaccharide derivative, the polycarboxylic acid and water. In a preferred embodiment, the solution consists essentially of carboxymethylcellulose, citric acid and water.

In another embodiment, the solution consists essentially of carboxymethylcellulose, hydroxyethylcellulose, citric acid and water. In yet another embodiment, the solution consists essentially of hydroxyethylcellulose, citric acid and water. The water is preferably purified water, such as distilled or deionized water. In this embodiment, the process is conducted in the substantial absence of any other agent that may affect the pH. In embodiments, the solution is substantially free of a molecular spacer, as this term is used in WO 2009/021701, including saccharides, polyols and sugar alcohols, such as sorbitol.

In another embodiment, the solution comprises a molecular spacer, preferably a polyhydroxylated compound, such as a saccharide, a polyol or a sugar alcohol. In one embodiment the molecular spacer is sorbitol. Preferably, the concentration of the molecular spacer is from 0% to about 20% by weight relative to the weight of the water. In one embodiment the concentration of the molecular spacer is from about 0.1% to about 20% by weight relative to the weight of the water. In another embodiment the concentration of the molecular spacer is from about 4% to about 20% or about 8% to 20% by weight relative to the weight of the water. In another embodiment, the concentration of the molecular spacer is less than 0.5% by weight relative to the weight of the water, for example, less than 0.4%, 0.3%, 0.2% or 0.1%. In certain embodiments at lower concentrations of the polycarboxylic acid, a fraction of the polysaccharide derivative is not crosslinked at the end of the process and can be washed out of the product hydrogel. In this case, the excess polysaccharide derivative serves as a molecular spacer. This can occur, for example, when the polysaccharide derivative is carboxymethylcellulose and the polycarboxylic acid is citric acid, at a citric acid concentration of about 0.5 or less, about 0.35% or less or about 0.3% or less by weight relative to the carboxymethylcellulose.

The cross-linking reaction is preferably conducted in the substantial absence of a catalyst. In a preferred embodiment, the cross-linking reaction is conducted in the substantial absence of sodium hypophosphite.

DETAILED DESCRIPTION OF THE INVENTION

The present invention provides polymer hydrogels, methods of preparing the polymer hydrogels, methods of use of the polymer hydrogels and articles of manufacture comprising the polymer hydrogels. In certain embodiments, the invention relates to the discovery that polysaccharide hydrogels, such as carboxymethylcellulose chemically cross-linked with citric acid, having advantageous properties can be prepared using a lower relative amount of polycarboxylic acid than has been taught in the art.

In one embodiment, the method of producing a polymer hydrogel comprises the steps of: (1) preparing an aqueous solution of the water soluble polysaccharide derivative and the polycarboxylic acid; (2) optionally agitating the solution; (3) isolating a polysaccharide derivative/polycarboxylic acid composite from the solution; and (4) heating the polysaccharide derivative/polycarboxylic acid composite at a temperature of at least about 80° C., or at least about 100° C., thereby cross-linking the polysaccharide with the polycarboxylic acid and forming the polymer hydrogel. In one embodiment, the polysaccharide derivative/polycarboxylic acid composite is granulated prior to conducting step (4) and optionally sieved to obtain particles of a desired size range. In one embodiment, the polymer hydrogel product of step (4) is granulated, for example, by grinding or milling, and optionally sieved.

In a preferred embodiment, the method of the invention includes the steps of (1) preparing an aqueous solution of the water soluble polysaccharide derivative and the polycarboxylic acid; (2) agitating the solution; (3) heating the solution to remove water and produce a polysaccharide derivative/polycarboxylic acid composite; (3a) granulating the polysaccharide derivative/polycarboxylic acid composite to produce composite particles; (4) heating the composite particles at a temperature of at least about 80° C., thereby cross-linking the polysaccharide derivative with the polycarboxylic acid and forming the polymer hydrogel; (5) washing the polymer hydrogel; (6) drying the polymer hydrogel and, optionally, (7) granulating the polymer hydrogel to produce hydrogel particles. The hydrogel particles produced in either or both of steps (3a) and (7) can be sieved to yield a sample of particles within a specified size range.

The term "polysaccharide derivative/polycarboxylic acid composite" or "composite" as used herein, refers to a substantially dry material comprising a mixture of the polysaccharide derivative and the polycarboxylic acid. In embodiments in which this composite is produced by evaporative drying of the aqueous solution of polysaccharide derivative and the polycarboxylic acid, the composite is the substantially dry residue which remains following removal of the unbound water. The composition can retain bound water, and can be, for example, up to 5, 10 or 20% water by weight.

Figure 1:
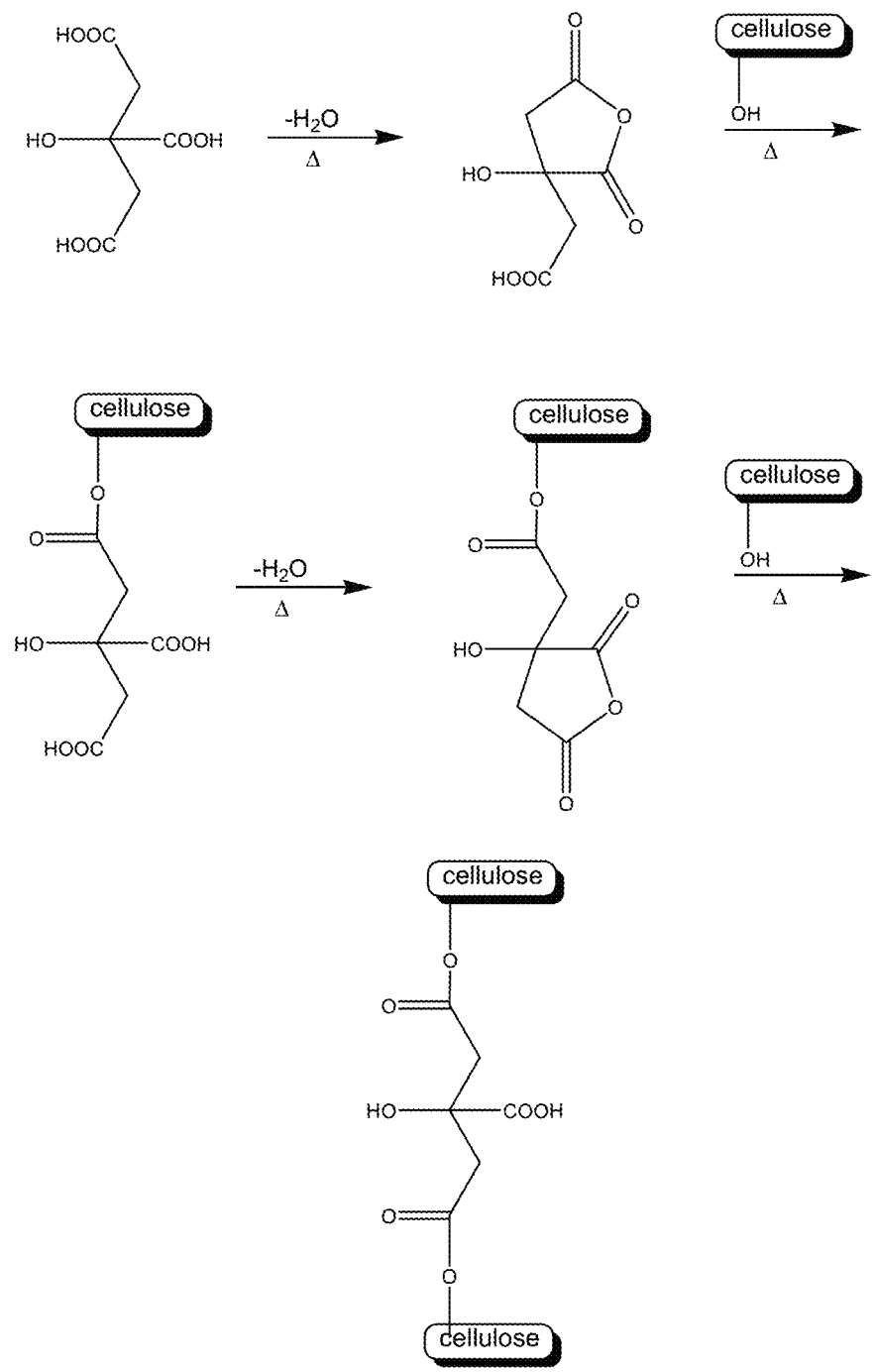
FIG. 1 illustrates the mechanism of cross-linking of a cellulosic polymer by citric acid.

Without being bound by theory, it is believed that the preparation of polymer hydrogels as disclosed herein proceeds via covalent cross-linking of the polysaccharide derivative with the polycarboxylic acid. FIG. 1 illustrates the cross-linking of a soluble cellulose derivative, such as carboxymethylcellulose, with citric acid. In this mechanism, the C1-carboxyl group of citric acid is activated by anhydride formation at neutral pH and at elevated temperature and in the presence of a very small amount of water, and in the absence of catalyst reacts with a cellulosic hydroxyl group to form an ester. The C5 carboxyl group is then activated by anhydride formation and reacts with a hydroxyl group of another cellulosic polymer chain, thereby forming a covalent chemical cross-link. Removal of water from the polysaccharide derivative/polycarboxylic acid solution before crosslinking is thus necessary to allow the anhydride formation/esterification reaction to occur. This is performed in steps (3) and (4) described above. As shown in Example 6 below, failure to remove the water from the solution prior to crosslinking results in hydrogels with physical cross-links instead of chemical cross-links.

The water-soluble polysaccharide derivative is preferably a carboxyalkyl polysaccharide, a hydroxyalkylpolysaccharide or a combination thereof. In certain embodiments, the water-soluble polysaccharide derivative is a cellulose derivative, such as a hydroxyalkylcellulose, for example, hydroxyethylcellulose, or a carboxyalkyl cellulose, including carboxymethylcellulose, carboxyethyl cellulose, and the like, or a mixture thereof. Preferably the polysaccharide derivative is carboxymethylcellulose or a salt thereof, such as the sodium salt. In certain embodiments, the polysaccharide derivative consists essentially of carboxymethylcellulose. In other embodiments, the polysaccharide derivative is a combination of carboxymethylcellulose with another polysaccharide derivative, such as another cellulose derivative, including a hydroxyalkylcellulose.

Methods of making carboxyalkyl cellulose are known to those skilled in the art. Suitably, a cellulosic material such as wood pulp fluff, cotton, cotton linters, and the like is provided. The cellulosic material may be in the form of fibers or fibers which have been comminuted to particulate form. The cellulosic material is dispersed in an inert solvent such as an alcohol and a carboxyalkylating agent is added to the dispersion. Carboxyalkylating agents generally comprise a chloroalkanoic acid such as monochloroacetic acid and sodium hydroxide. It is possible to perform the carboxyalkylation of the starting polysaccharide in such a manner that the solution of carboxyalkyl cellulose and water is formed directly. That is, the carboxyalkylation process may be performed in an aqueous medium such that, upon formation of the carboxyalkyl cellulose, it is solubilized in the water. In this manner, no recovery step is necessary between formation of the carboxyalkyl cellulose and the formation of the solution of carboxyalkyl cellulose and water.

The carboxymethylcellulose or salts thereof preferably have an average degree of substitution from about 0.3 to about 1.5, more preferably from about 0.4 to about 1.2. The degree of substitution refers to the average number of carboxyl groups present on the anhydroglucose unit of the cellulosic material. Carboxymethylcelluloses having an average degree of substitution within the range of from about 0.3 to about 1.5 are generally water-soluble. As used herein, a carboxyalkyl cellulose, such as carboxymethylcellulose, is considered to be "water-soluble" when it dissolves in water to form a true solution.

Carboxymethylcellulose is commercially available in a wide range of molecular weights. Carboxymethylcellulose having a relatively high molecular weight is preferred for use in the present invention. It is generally most convenient to express the molecular weight of a carboxymethylcellulose in terms of its viscosity in a 1.0 weight percent aqueous solution. Carboxymethylcelluloses suitable for use in the present invention preferably have a viscosity in a 1.0 weight percent aqueous solution from about 50 centipoise to about 10,000 centipoise, more preferably from about 500 centipoise to about 10,000 centipoise, and most preferably from about 1,000 centipoise to about 2,800 centipoise. In one preferred embodiment, the carboxymethylcellulose has a weighted average molecular weight of 500 to 800 Kd.

Suitable carboxyalkyl celluloses are commercially available from numerous vendors. An example of a commercially available carboxyalkyl cellulose is carboxymethylcellulose, commercially available from Ashland/Aqualon Company under the trade designation AQUALON™, Blanose and BONDWELL™ depending on the geographical region in which it is sold. The polycarboxylic acid is preferably an organic acid containing two or more carboxyl (COOH) groups and from 2 to 9 carbon atoms in the chain or ring to which the carboxyl groups are attached; the carboxyl groups are not included when determining the number of carbon atoms in the chain or ring (e.g., 1,2,3 propane tricarboxylic acid would be considered to be a C3 polycarboxylic acid containing three carboxyl groups and 1,2,3,4 butanetetracarboxylic acid would be considered to be a C4 polycarboxylic acid containing four carboxyl groups). Alternatively, a heteroatom such as an oxygen atom or a sulfur atom, can substitute for a methylene group in the polycarboxylic acid. More specifically, the polycarboxylic acids preferred for use as cross-linking agents in the present invention include aliphatic and alicyclic acids which are either saturated or olefinically unsaturated, with at least three carboxyl groups per molecule or with two carboxyl groups per molecule and a carbon-carbon double bond present alpha, beta to one or both carboxyl groups. It is further preferred that the polycarboxylic acid have a carboxyl group in an aliphatic or alicyclic polycarboxylic acid which is separated from a second carboxyl group by 2 or 3 carbon atoms. Without being bound by theory, it is believed that a carboxyl group of the polycarboxylic acid can preferably form a cyclic 5- or 6-membered anhydride ring with a neighboring carboxyl group in the polycarboxylic acid molecule. Where two carboxyl groups are separated by a carbon-carbon double bond or are both connected to the same ring, the two carboxyl groups must be in the cis configuration relative to each other to interact in this manner.

Suitable polycarboxylic acids include citric acid (also known as 2-hydroxy-1,2,3 propane tricarboxylic acid), tartrate monosuccinic acid, oxydisuccinic acid also known as 2,2'-oxybis(butanedioic acid), thiodisuccinic acid, disuccinic acid, maleic acid, citraconic acid also known as methylmaleic acid, citric acid, itaconic acid also known as methylenesuccinic acid, tricarboxylic acid also known as 1,2,3 propane tricarboxylic acid, transaconitic acid also known as trans-1-propene-1,2, 3-tricarboxylic acid, 1,2,3,4-butanetetracarboxylic acid, all-cis-1,2,3,4-cyclopentanetetracarboxylic acid, mellitic acid also known as benzenehexacarboxylic acid, and oxydisuccinic acid also known as 2,2'-oxybis(butanedioic acid). A more detailed description of tartrate monosuccinic acid, tartrate disuccinic acid, and salts thereof, can be found in Bushe et al., U.S. Pat. No. 4,663,071, incorporated herein by reference.

Preferably, the polycarboxylic acid is saturated and contains at least three carboxyl groups per molecule. A preferred polycarboylic acid is citric acid. Other preferred acids include 1,2,3 propane tricarboxylic acid, and 1,2,3,4 butane tetracarboxylic acid. Citric acid is particularly preferred, since it provides hydrogels with high levels of wettability, absorbency and resiliency which are safe and non-irritating to human tissue, and provides stable, cross-link bonds. Furthermore, citric acid is available in large quantities at relatively low prices, thereby making it commercially feasible for use as the cross-linking agent.

The above list of specific polycarboxylic acids is for exemplary purposes only, and is not intended to be all inclusive. Importantly, the cross-linking agent must be capable of reacting with at least two hydroxyl groups on proximately located cellulose chains of two adjacent cellulose molecules. One of skill in the art will recognize that the aliphatic and alicyclic $C_2$-$C_9$ polycarboxylic acid cross-linking agents described above may be reacted in a variety of forms to produce the cross-linked polymer hydrogels herein, such as the free acid form and salts thereof. Although the free acid form is preferred, all such forms are meant to be included within the scope of the invention.

In one embodiment, the polysaccharide derivative and the polycarboxylic acid are both food grade or pharmaceutical grade materials. For example, carboxymethylcellulose and citric acid are both used as food additives and pharmaceutical excipients and are, therefore, available in forms which are suitable for these uses.

The term "carboxymethylcellulose" (CMC), as used herein, refers to carboxymethylcellulose (cellulose carboxymethyl ether) in the acid form, as a salt or as a combination of the acid form and a salt. Preferred salt forms include sodium carboxymethylcellulose and potassium carboxymethylcellulose. In particularly preferred embodiments, the carboxymethylcellulose is present in the solution as the sodium salt (NaCMC).

The aqueous solution of the cellulose derivative and the polycarboxylic acid can be formed at any temperature at which the cellulose derivative is soluble in the water. Generally, such temperatures will be within the range of from about 10° C. to about 100° C. Preferably, the solution is prepared substantially at room temperature, for example, between 20° C. and 30° C.

It is preferred to have the solution pH between 5 and 8, more preferably between 6 and 7.

The polysaccharide derivative/polycarboxylic acid composite isolated from the aqueous solution is suitable for chemical cross-linking to form polymer hydrogels having improved absorption properties due to the inter-chain entanglements. Without being bound by theory, it is believed that solubilization provides for molecular entanglements which produce a tighter network and a preferred distribution of the carboxyl groups and hydroxyl groups between the polysaccharide derivative and the polycarboxylic acid. Greater entanglement of the polysaccharide derivative chains thus results in a more uniform cross-linking upon heat-treatment, resulting, in turn in a super-absorbent polymer hydrogel with a greater media uptake capacity and significantly improved mechanical and rheological properties.

The polysaccharide derivative/polycarboxylic acid composite can be isolated from the solution by any method that avoids substantial deterioration of the absorption characteristics of the resulting polymer hydrogel. Examples of such methods include evaporative drying, freeze drying, precipitation, centrifugation, spray drying, critical point drying, and the like.

Preferably the polysaccharide derivative/polycarboxylic acid composite is isolated by evaporative drying at a temperature within the range from about 10° C. to about 100° C., preferably from about 45° C. to about 80° C. In certain embodiments, drying is conducted at an initial temperature greater than 80° C., for example, from 80° C. to 100° C., to substantially reduce the solution volume, then the temperature is reduced below 80° C. to complete the drying. For example, the solution can be dried initially at 85° C., and then the temperature can be reduced to 50° C. to complete the drying. Naturally, higher temperatures can be employed if the solution is placed under pressure. Lower temperatures can be employed if the solution is placed under a vacuum.

In one preferred embodiment, evaporative drying is conducted at a temperature of about 70° C.

When the solution is dried by heating, the step of isolating the polysaccharide derivative/polycarboxylic acid composite and the step of crosslinking the composite can be combined in a single step, preferably with a temperature change. For example, the drying step can be conducted at a first temperature and then the temperature can be raised to a second, higher, temperature once drying is complete. Alternatively, the solution can be dried initially at a higher temperature, for example from about 80° C. to about 100° C. and then, before drying is complete the temperature can be reduced below 80° C. to complete drying. The temperature can then be raised to greater than 80° C. to initiate cross-linking. In one embodiment, drying is conducted at an initial temperature of about 85° C., the temperature is reduced to about 50° C. before drying is complete and then, upon completion of drying, the temperature is raised to about 120° C.

Other methods of isolation of the composite include precipitation in which a precipitating agent (non-solvent), such as methanol, ethanol or acetone is added to the aqueous solution to precipitate the composite from solution. The composite can then be recovered by filtration. If precipitation is used to recover the composite, the composite is optionally washed with water to remove the precipitating agent. Depending on the form in which the composite is recovered, it may be necessary or desirable to alter its form prior to the cross-linking step. For example, if evaporative drying is employed, the composite may be recovered in the form of a film or sheet. This film or sheet material can then be granulated, fragmented, ground or comminuted into composite particles, flakes or granules prior to the cross-linking step. In one embodiment, the composite particles are substantially spherical.

If evaporative drying by spray drying is employed, the composite may be recovered in the form of particles, flakes or granules prior to the cross-linking step.

In one embodiment, the composite particles are substantially spherical. In another embodiment, the particles are substantially irregular in form.

The composite particles preferably have a maximum cross-sectional diameter or greatest dimension within the range from about 5 micrometers to about 2,000 micrometers, preferably within the range from about 100 micrometers to about 1,000 micrometers, and preferably the average particle cross-sectional diameter should be from about 300 micrometers to about 800 micrometers.

Without being bound by theory, it is believed that the step of granulating the composite prior to cross-linking provides a homogeneous distribution of cross-linking sites as well as enhanced water evaporation before the crosslinking reaction begins, resulting in a material with high conservative modulus (G') and uniform chemical stabilization. This is due to the fact that the thermal gradient in finely granulated particles is more homogeneous than in the bulk structure, resulting in uniform cross-linking kinetics and efficiency. This also eliminates the problem of the formation of stiffer and weaker areas in the final product, related to higher or lower, respectively, cross-linking degrees. This effect may cause the additional problem of the formation of a residual stress in the hydrogel bulk corresponding to surfaces of differing stiffness, which can in turn lead to delamination of the material during media uptake, in addition to the already cited decrease in G'.

The isolated polysaccharide derivative/polycarboxylic acid composite is heat-treated at an elevated temperature to cross-link the polysaccharide derivative. Any combination of temperature and time which achieves a desired degree of cross-linking, without undesirable damage to the polysaccharide derivative, is suitable for use in the present invention. Preferably the composite is maintained at a temperature of 80° C. or greater, for example, 100° C. or greater. In certain embodiments, the temperature is within the range from about 100° C. to about 250° C., preferably from about 120° C. to about 200° C., and more preferably from about 120° C. to about 170° C. In a particularly preferred embodiment, the composite is maintained at about 120° C. The higher the temperature that is employed, the shorter the period of time necessary to achieve the desired degree of cross-linking. Generally, the heat-treating process will extend over a time period within the range of from about 1 minute to about 600 minutes, preferably from about 1 minute to about 240 minutes, and more preferably from about 5 minutes to about 120 minutes.

The heat-treating process causes the polysaccharide derivative chains to cross-link via the polycarboxylic acid and become water-insoluble. The heat-treating process desirably produces a polymer hydrogel having the ability to absorb aqueous liquids, in particular stomach fluids which have high salinity and low pH.

Any combination of time and temperature which produces a polymer hydrogel having a desired absorbance of an aqueous medium of interest can be used in the present invention. The ability of a polymer hydrogel to absorb an aqueous medium is indicated by its Free Swell Capacity or its media uptake ratio for the medium of interest. The term "Free Swell Capacity" refers to the amount, in grams, of a specified aqueous medium which 1 gram of the dried polymer hydrogel can absorb at 37° C. in 60 minutes under no load. Preferably, the polymer hydrogel of the invention has a Free-Swell Capacity of at least about 50 grams, more preferably of at least about 70 gram, and most preferably of at least about 100 gram in an aqueous solution containing about 11% simulated gastric fluid (SGF/water=1:8). The procedure for determining the Free-Swell Capacity is set forth below in the examples.

The media uptake ratio (MUR) is another measure of the ability of the polymer hydrogel to absorb water or a specified aqueous solution at a particular temperature. The MUR is obtained through swelling measurements at equilibrium (using, for example, a Sartorius micro scale with a sensitivity of $10^{-5}$ g) and it is calculated with the following formula $MUR=W_s/W_d$, wherein $W_s$ is the weight of the polymer hydrogel after immersion in distilled water or the specified media until equilibrium is reached, 24 hours unless otherwise specified. Unless otherwise specified, the MUR is determined at room temperature, or about 25° C. $W_d$ is the weight of the polymer hydrogel before immersion, the polymer hydrogel having been previously dried in order to remove any residual water.

In a preferred embodiment, the method for preparing a polymer hydrogel of the invention comprises the steps of (a) providing an aqueous solution consisting essentially of: (a) a cellulose derivate, such as carboxymethylcellulose or a salt thereof, or hydroxyethylcellulose or a combination thereof, a polycarboxylic acid, such as citric acid, and water; (b) stirring the aqueous solution; (c) evaporating the free water from the solution to produce a dried polymer/carboxylic acid composite; (d) grinding the dried composite to form composite particles; and (e) heating the composite particles to a temperature of at least about 80° C. or at least about 100° C., thereby cross-linking the cellulose derivative and forming a polymer hydrogel.

In certain embodiments, the product of step (e) is ground to produce particles and the particles are optionally sieved. This is particularly desirable in cases in which step (e) causes agglomeration of particles produced in step (d). The particles can be sieved to yield a sample comprising particles within a desired size range. The size of the particles can, for example, affect the amount of hydrogel that can fit within a capsule for an oral dosage form. The particle size also affects the rheological properties, such as the elastic modulus, and the swelling kinetics of the hydrogel. In one embodiment, the hydrogel consists substantially of particles in the size range from 1 μm to 2000 μm, preferably from 10 μm to 2000 μm, and more preferably from 100 μm to 1000 μm. A sample of hydrogel consists substantially of particles in a specified size range when the hydrogel is greater than 50% by mass particles in the specified size range. Preferably, the hydrogel is at least 60%, 70%, 80%, 90% or 95% by mass particles in the specified size range.

The cellulose derivative is preferably present in the aqueous solution at a concentration of 4% or greater, preferably from about 4% to about 8%, 5% to about 7%, 5.5% to about 6.5% or about 6% by weight relative to the weight of the water used to prepare the solution. Preferably the polycarboxylic acid is present in the solution at a concentration of about 0.5% or less, more preferably, about 0.35% or less or about 0.3% or less by weight relative to the weight of the cellulose derivative. Preferably the cellulose derivative is carboxymethylcellulose at a concentration of about 5% to about 7%, more preferably about 5.5% to about 6.5% and most preferably about 6% by weight relative to water, and the polycarboxylic acid is citric acid, at a concentration of about 0.15% to about 0.35%, preferably about 0.2% to about 0.35%, 0.15% to about 0.3% or about 0.3% by weight relative to carboxymethylcellulose.

The pH of the aqueous solution is preferably maintained from about 5 to about 9, from about 6 to 8, from about 6.5 to about 7.5 or about 5.5 to about 7.

In one embodiment of the method of the invention, the aqueous solution is dried to form the dried composite as a sheet, which is ground to form composite particles. Preferably the composite particles have a greatest dimension between 10 μm and 1000 μm, more preferably between 100 μm and 1000 μm with an average size of between 300 μm and 600 μm. The composite particles are optionally sieved to provide particles in a desired size range. The composite particles are cross-linked at elevated temperature, preferably 80° C. or higher or 100° C. or higher. In preferred embodiments, the resulting particles are substantially homogeneously cross-linked. It is believed that cross-linking in a particle shape creates a preferential tighter cross-linked outer boundary for the particle that improves the particle's elasticity and still maintains good water absorbency capability in the core of the particles.

The time required to cross-link the particles depends upon the cross-linking temperature and the concentration of the polycarboxylic acid. For example, at a citric acid concentration of 0.3% (w/w vs. carboxymethylcellulose) it takes about 2-10 minutes at 180° C. or 2-5 hours at 120° C. to cross-link the carboxymethylcellulose. At 80° C. it takes 4 hours with a citric acid concentration of 2.5% (w/w) or 20 hours with a citric acid concentration of 1% (w/w).

Steps (b)-(e) of the process can take place in a single operation. The solution of step (a) can be, for example, spray dried. That is, the solution can be sprayed into a chamber to form droplets which are dried and cross-linked by a stream of hot air. In this embodiment, the solution is fragmented prior to formation of the composite.

In one embodiment, the composite is isolated from the aqueous solution by substantially drying the aqueous solution, for example, by heating, as described above.

In preferred embodiments, the aqueous solution is placed on a tray, such as a stainless steel, polypropylene or Teflon tray, prior to isolating the composite. This increases the surface area of the solution, facilitating the evaporation of the water. In an embodiment, the solution is maintained at elevated temperature until it begins to form a solid or semi-solid, for example, with formation of a gel. The gel is optionally then inverted in the tray, and heating is continued to substantial dryness. The heating preferably can be conducted in a suitable oven or vacuum oven.

The composite is granulated, for example by grinding, milling or fragmenting, to form composite particles and the particles are maintained at elevated temperature, thereby effecting cross-linking and producing polymer hydrogel particles. Preferably, the cross-linking step (e) is conducted at a temperature of about 80° or greater or about 100° C. or greater, more preferably from about 100° C. to about 160° C., and still more preferably, about 115° C. to about 125° C., or about 120° C.

In preferred embodiments, the substantially dry composite is ground to form particles of a suitable size. The ground particles are placed on a tray, such as a stainless steel tray or placed in a rotating oven. This increases the surface area, facilitating the preferentially surface cross-linking reaction. In an embodiment, the particles are maintained at elevated temperature according to step (e) until cross-linking is complete. The heating preferably is conducted in a suitable oven or vacuum oven.

The ground particles are optionally sized, for example by sieving, prior to or following the cross-linking step, to obtain particles within a desired size range.

The methods of the invention can further include the steps of purifying the polymer hydrogel, for example, by washing the polymer hydrogel in a polar solvent, such as water, a polar organic solvent, for example, an alcohol, such as methanol or ethanol, or a combination thereof. The polymer hydrogel immersed in the polar solvent swells and releases impurities, such as by-products or unreacted citric acid. Water is preferred as the polar solvent, distilled and/or deionized water is still more preferred. The volume of water used in this step is preferably at least the volume to reach the maximum media uptake degree of the gel, or at least approximately 2- to 20-fold greater than the initial volume of the swollen gel itself. The polymer hydrogel washing step may be repeated more than once, optionally changing the polar solvent employed. For example, the polymer hydrogel can be washed with methanol or ethanol followed by distilled water, with these two steps optionally repeated one or more times.

The polymer hydrogel can further be dried to remove most or substantially all water.

In one embodiment, the drying step is carried out by immersing the fully swollen polymer hydrogel in a cellulose non-solvent, a process known as phase inversion. A "cellulose non-solvent", as this term is used herein, is a liquid compound which does not dissolve the cellulose derivative and does not swell the polymer hydrogel, but is preferably miscible with water. Suitable cellulose non-solvents include, for example, acetone, methanol, ethanol, isopropanol and toluene. Drying the polymer hydrogel by phase inversion provides a final microporous structure which improves the absorption properties of the polymer hydrogel by capillarity. Moreover, if the porosity is interconnected or open, i.e. the micropores communicate with one another, the absorption/desorption kinetics of the gel will be improved as well. When a completely or partially swollen gel is immersed into a nonsolvent, the gel undergoes phase inversion with the expulsion of water, until the gel precipitates in the form of a vitreous solid as white coloured particles. Various rinses in the non-solvent may be necessary in order to obtain the dried gel in a short period of time. For example, when the swollen polymer hydrogel is immersed in acetone as the non-solvent, a water/acetone mixture is formed which increases in water content as the polymer hydrogel dries; at a certain acetone/water concentration, for example, about 55% in acetone, water is no longer able to exit from the polymer hydrogel, and thus fresh acetone has to be added to the polymer hydrogel to proceed with the drying process. Increasing the acetone/water ratio during drying increases the rate of drying. Pore dimensions are affected by the rate of the drying process and the initial dimensions of the polymer hydrogel particles: larger particles and a faster process tend to increase the pore dimensions; pore dimensions in the microscale range are preferred, as pores in this size range exhibit a strong capillary effect, resulting in the higher sorption and water retention capacity.

In other embodiments, the polymer hydrogel is not dried by phase inversion. In these embodiments, the polymer hydrogel is dried by another process, such as air drying, vacuum drying, freeze drying or by drying at elevated temperature, for example, in an oven or vacuum oven. These drying methods can be used alone or in combination. In certain embodiments, these methods are used in combination with the non-solvent drying step described above. For example, the polymer hydrogel can be dried in a non-solvent, followed by air drying, freeze drying, oven drying, or a combination thereof to eliminate any residual traces of nonsolvent. Oven drying can be carried out at a temperature of, for example, approximately 30-45° C. until the water or residual non-solvent is completely removed. The washed and dried polymer hydrogel can then be used as is, or can be milled to produce polymer hydrogel particles of a desired size.

In preferred embodiments, the cellulose derivative is carboxymethylcellulose, more preferably carboxymethylcellulose sodium salt. In another embodiment, the cellulose derivative is hydroxyethylcellulose.

In another embodiment, the cellulose derivative is a combination of carboxymethylcellulose and hydroxyethylcellulose. The weight ratio of carboxymethylcellulose to hydroxyethylcellulose can be from about 1:10 to about 10:1. Preferably the weight ratio of carboxymethylcellulose to hydroxyethylcellulose is about 1 or less, more preferably, from about 1:5 to about 1:2, more preferably about 1:3.

One particularly preferred embodiment of the method of the invention comprises the following steps: Step 1, carboxymethylcellulose sodium salt and citric acid are dissolved in purified water to produce a solution essentially consisting of about 5% to about 7%, preferably about 6%, carboxymethylcellulose by weight relative to the weight of water, and citric acid in an amount of about 0.15% to about 0.35% or about 0.15% to about 0.30% by weight relative to the weight of carboxymethylcellulose; Step 2, maintaining the solution at a temperature from about 40° C. to about 70° C. or 40° C. to about 80° C., preferably about 70° C., to evaporate the water and form a substantially dry carboxymethylcellulose/citric acid composite; Step 3, grinding the composite to form composite particles; and Step 4, maintaining the composite particles at a temperature from about 80° C. to about 150° C. or about 100° C. to about 150° C., preferably, about 120° C., for a period of time sufficient to achieve the desired degree of cross-linking and form the polymer hydrogel. The method can optionally further include Step 5, washing the polymer hydrogel with purified water; and Step 6, drying the purified polymer hydrogel at elevated temperature.

The present invention also provides polymer hydrogels which can be prepared using the methods of the invention. Such polymer hydrogels comprise cross-linked carboxymethylcellulose, hydroxyethylcellulose or a combination of carboxymethylcellulose and hydroxyethylcellulose. In a preferred embodiment, the polymer hydrogel consists essentially of citric acid cross-linked carboxymethylcellulose.

In another embodiment, the present invention provides polymer hydrogels, including superabsorbent polymer hydrogels, which can be prepared using the methods of the invention. The invention includes articles of manufacture, pharmaceutical compositions, foods, foodstuffs and medical devices, agriculture and horticulture products, personal hygiene products which comprise such polymer hydrogels. The invention further includes methods of use of the polymer hydrogels of the invention for the preparation of foods and the treatment of obesity.

In certain embodiments, polymer hydrogels produced by the methods described herein form xerogels that have greater density than carboxymethylcellulose xerogels produced using other methods, while retaining significant absorption properties.

The methods of the invention produce polymer hydrogels which combine both physical and chemical cross-linking and which have good mechanical properties, long term stability in dry and swollen form and good retention capacity and biocompatibility. [Demitri et al., *Journal of Applied Polymer Science*, Vol. 110, 2453-2460 (2008)]. The polymer hydrogels of the invention exhibit good media uptake properties in the free state, high bulk density, and cost effective production. Further, the polymer hydrogels have rapid media uptake kinetics in body fluids.

In preferred embodiments, the polymer hydrogels of the invention have a media uptake ratio in distilled water of at least about 20, about 30, about 40, about 50, about 60, about 70, about 80, about 90 or about 100. For example, in certain embodiments, the polymer hydrogels of the invention have a media uptake ratio in distilled water from about 20 to about 1000, from about 20 to about 750, from about 20 to about 500, from about 20 to about 250, from about 20 to about 100. In certain embodiments, the polymer hydrogels of the invention have a media uptake ratio in distilled water from about 20, 30, 40, 50, 60, 70, 80, 90 or 100 to about 120, 150, 200, 300, 400, 500, 600, 700, 800, 900, 1000 or greater, or within any range bounded by any one of these lower limits and any one of these upper limits.

In certain embodiments, the polymer hydrogels of the invention can absorb an amount of one or more bodily fluids, such as blood, blood plasma, urine, intestinal fluid or gastric fluid, which is at least 10, 20, 30, 40, 50, 60, 70, 80, 90, or 100 times their dry weight. The ability of the polymer hydrogel to absorb bodily fluids can be tested using conventional means, including testing with samples of bodily fluids obtained from one or more subjects or with simulated bodily fluids, such as simulated urine or gastric fluid. In certain preferred embodiments, the polymer hydrogels can absorb significant amounts of a fluid prepared by combining one volume of simulated gastric fluid (SGF) with eight volumes of water. SGF can be prepared using USP Test Solutions procedures which are known in the art. In some embodiments, the polymer hydrogels of the invention have a media uptake ratio of 10, 20, 30, 40, 50, 60, 70, 80, 90, 100, or 150 in SGF/water (1:8). In some embodiments the polymer hydrogels of the invention have a media uptake ratio of 10 to 300, from 20 to 250, from 30 to 200, from 50 to 180 or from 50 to 150 in SGF/water (1:8). In preferred embodiments the hydrogel has a media uptake ratio of 50 or greater in SGF/water (1:8).

The polymer hydrogels of the invention include cross-linked polymers having varying extents of hydration. For example, the polymer hydrogels can be provided in a state of hydration ranging from a substantially dry or anhydrous state, such as a xerogel or a state in which from about 0% to about 5% or up to about 10% of the polymer hydrogel by weight is water or an aqueous fluid, to states comprising a substantial amount of water or aqueous fluid, including up to a state in which the polymer hydrogel has absorbed a maximum amount of water or an aqueous fluid.

In an embodiment, the polymer hydrogels of the invention are preferably glassy but amorphous or vitreous materials when in a substantially dry or xerogel form. In an embodiment, the polymer hydrogels of the invention have a tapped density of greater than about 0.5 g/cm³. In preferred embodiments, the tapped density is from about 0.55 to about 0.8 g/mL when determined as described in US Pharmacopeia <616>, incorporated herein by reference. In a preferred embodiment, the tapped density is about 0.6 g/cm³ or greater, for example, from about 0.6 g/cm³ to about 0.8 g/cm³.

A preferred hydrogel of the invention consists of carboxymethylcellulose cross-linked with citric acid. Preferably the hydrogel has a water content of less than about 10% by weight, a tapped density of at least about 0.6 g/mL, an elastic modulus of at least about 350 Pa, or a media uptake ratio in SGF/water 1:8 of at least about 50. More preferably the polymer hydrogel has each of the foregoing properties. In a particularly preferred embodiment, the polymer hydrogel consists of particles which are substantially in the size range of 100 µm to 1000 µm. In one embodiment, at least about 95% of the hydrogel by weight consists of particles in the size range of 100 µm to 1000 µm.

The degree of cross-linking (d.c.) of a cross-linked polymer is defined as the number density of junctions joining the polymer chains into a permanent structure. According to this definition the degree of cross-linking is given by:

$$d.c. = \frac{\upsilon}{2V} \quad (\text{eq. 1})$$

where $\upsilon/2$ is the total number of chemical cross-links and V is the total volume of polymer.

The concentration of elastically effective chain elements, $\rho_x = \upsilon_e/V$, corresponds to the concentration of all chemically cross-linked polymer segments ($\upsilon/V$):

$$\rho_x = \frac{\upsilon_e}{V} = \frac{\upsilon}{V} = \frac{1}{\overline{\upsilon} \overline{M}_c} d.c. = \frac{\upsilon}{2V} \quad (\text{eq. 2})$$

where $\overline{\upsilon}$ is the specific volume of the polymer, $\overline{M}_c$ is the average molecular weight between cross-links, and $\upsilon_e/V$ is the moles of elastically effective chains per unit volume of network.

The degree of cross-linking can be evaluated by means of uniaxial compression measurements on the swollen hydrogel. In fact, a swollen hydrogel, when submitted to a uniaxial compressive load, displays a deformational behavior which depends upon the elastic response of deformed chains, upon the interaction among fixed charges and upon the free energy change associated with the release of some amount of absorbed water. By making the simplifying assumption that no volume change occurs upon compression of the swollen hydrogel, Flory derived a relationship between the compressive stress and the compressive deformation for the case of a swollen cross-linked polymer, based on the assumption of Gaussian statistics and of affine deformation obtaining:

$$\sigma = RT \frac{v_e}{V_0} \phi_{2,r}^{2/3} \phi_{2,s}^{1/3} \left( \alpha - \frac{1}{\alpha^2} \right) = G \left( \alpha - \frac{1}{\alpha^2} \right) \quad \text{(eq. 3)}$$

where $\sigma = F/A_0$ is the uniaxial compressive stress (where F is the traction force and $A_0$ is the initial area of swollen sample cross-section), $\alpha = L/L_i$ with L, the actual thickness of the compressed swollen sample and $L_i$, the initial thickness of the swollen sample, R, the universal gas constant, T, the absolute temperature, $\phi_{2,s}$, the polymer volume fraction in the swollen state under compression which is assumed to be equal to the value for the undeformed swollen gel, $v_e/V_0$, the moles of elastically effective chains per $cm^3$ of dry polymer network and G is the shear modulus of the swollen network. Example 5 describes the determination of the degree of cross-linking of samples of citric acid cross-linked CMC prepared using same concentrations of CMC and different amounts of citric acid. In certain embodiments in which a lower concentrations of citric acid is used, for example, less than about 0.5% or 0.4% citric acid by weight relative to carboxymethylcellulose, a fraction of the carboxymethylcellulose is not involved in cross-linked network formation and can be removed by washing from the hydrogel product.

The hydrogels of the invention preferably have a cross-linked and singly bonded citric acid to carboxymethylcellulose ratio of 0.05% to 1% wt/wt and more preferably a ratio of 0.1% to 0.4% wt/wt. Still more preferably, the crosslinked and singly bonded citric acid to carboxymethylcellulose ratio is 0.225% to 0.375% wt/wt.

The hydrogels of the invention preferably have a degree of cross-linking from about $2.5 \times 10^{-5}$ $mol/cm^3$ to about $5 \times 10^{-5}$ $mol/cm^3$, more preferably from about $4 \times 10^{-5}$ $mol/cm^3$ to about $5 \times 10^{-5}$ $mol/cm^3$.

The polymer hydrogels of the invention can be used in methods for treating obesity, reducing food or calorie intake or achieving or maintaining satiety. Hydrogels of the invention can also be used to improve glycemic control and to treat or prevent diabetes. The methods comprise the step of administering an effective amount of a polymer hydrogel of the invention to the stomach of a subject, preferably by oral administration, for example, by causing the subject, such as a mammal, including a human, to swallow the polymer hydrogel, optionally in combination with ingestion of a volume of water. Upon contacting water or aqueous stomach contents, the polymer hydrogel swells and occupies stomach volume decreasing the capacity of the stomach for food and/or the rate of food absorption. When ingested in combination with food, the polymer hydrogel increases the volume of the food bolus without adding to the calorie content of the food. The polymer hydrogel can be ingested by the subject prior to eating or in combination with food, for example, as a mixture of the polymer hydrogel with food.

Figure 2:
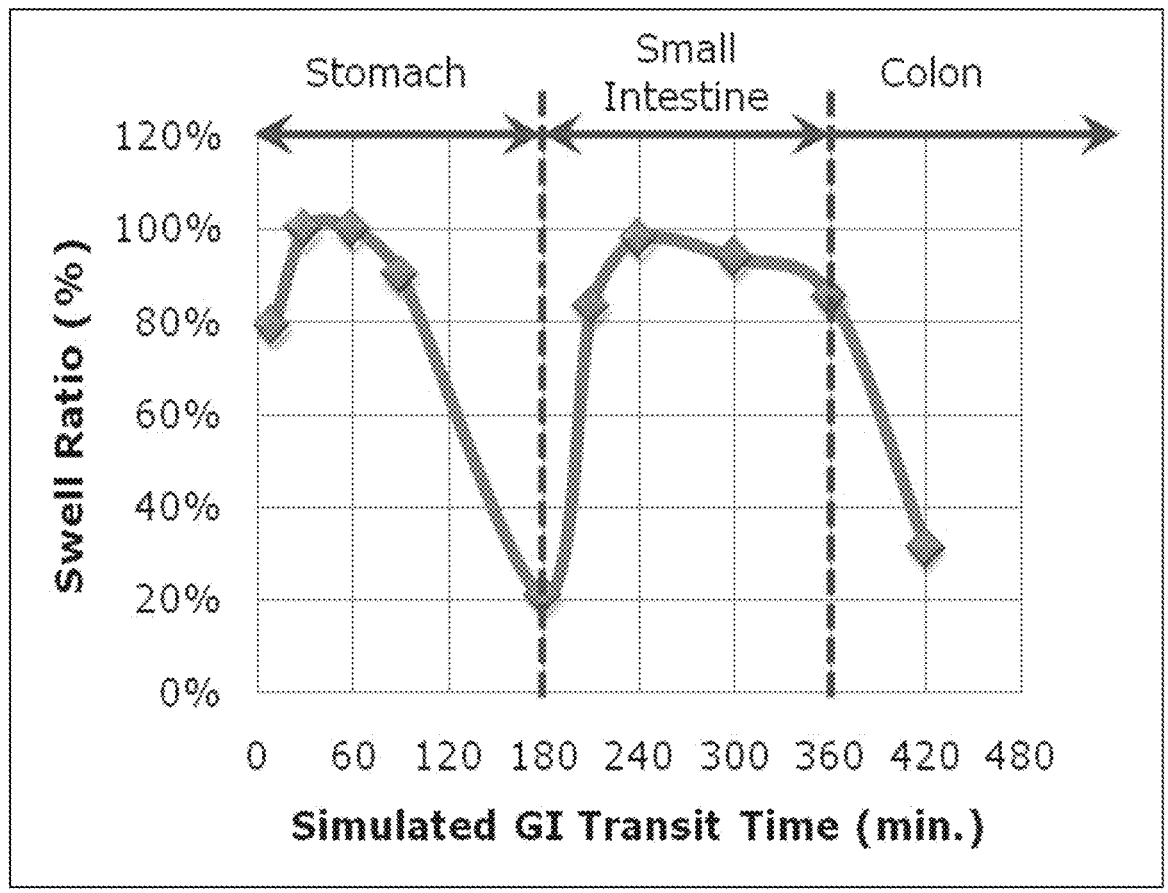
FIG. 2 is a graph showing the theoretical media uptake and collapse of an edible polymer hydrogel as it moves through the gastrointestinal tract.

The polymer hydrogel can be ingested alone, in a mixture with liquid or dry food or as a component of a food or edible matrix, in a dry, partially swollen or fully swollen state, but is preferably ingested in a state of hydration which is significantly below its fluid capacity, more preferably the polymer hydrogel is ingested in a substantially anhydrous state, that is, about 10% or less water by weight. The polymer hydrogel can be formulated for oral administration in a capsule, sachet or tablet or suspension. When administered in a substantially anhydrous form, the volume of the stomach taken up by the polymer hydrogel will be significantly greater than the volume of the polymer hydrogel ingested by the subject. The polymer hydrogels of the invention can also take up volume and/or exert pressure on the wall of the small intestine by moving from the stomach into the small intestine and media uptake. Preferably, the polymer hydrogel will remain swollen in the small intestine for a period of time sufficient to inhibit the intake of food by the subject, before shrinking sufficiently for excretion from the body. The time sufficient to inhibit the intake of food by the subject will generally be the time required for the subject to eat and for the ingested food to pass through the small intestine; Such shrinking can occur, for example, by degradation through loss of cross-links, releasing fluid and decreasing in volume sufficiently for excretion from the body. A schematic depicting the theoretical behaviour of such a hydrogel as it passes through the gastrointestinal tract is set forth in FIG. 2.

The polymer hydrogels of the invention preferably exhibit pH-dependent media uptake, with greater media uptake observed at higher pH than at lower pH. Thus, such a polymer will not swell significantly in the stomach unless food and/or water is present to raise the pH of the stomach contents and will move into the small intestine. When ingested with food, the polymer hydrogel preferably swells initially in the stomach, shrinks when the stomach is emptied of food and the pH drops and then moves from the stomach to the small intestine. In the higher pH environment of the small intestine the polymer hydrogel will swell again, taking up volume in the small intestine and/or exerting pressure on the wall of the small intestine.

The polymer hydrogel can optionally be administered in combination with a pH modifying agent, which is an agent which alters the pH of the microenvironment of the polymer hydrogel, thereby modifying its ability to absorb fluids. For example, for polymer hydrogels comprising an anionic polymer, agents which increase the pH of the microenvironment can increase the swellability of the polymer hydrogel. Suitable pH modifying agents for use with the polymer hydrogels of the invention include buffering agents, $H_2$ blockers, proton pump inhibitors, antacids, proteins, nutritional shakes, and combinations thereof. Suitable buffering agents and antacids include ammonium bicarbonate, sodium bicarbonate, calcium carbonate, calcium hydroxide, aluminium hydroxide, aluminium carbonate, magnesium carbonate, magnesium hydroxide, potassium bicarbonate, potassium carbonate, potassium hydroxide, sodium carbonate, sodium hydroxide and combinations thereof. Suitable $H_2$ blockers include cimetidine, ranitidine, famotidine, nizatidine and combinations thereof. Suitable proton pump inhibitors include omeprazole, lansoprazole, esomeprazole, pantoprazole, abeprazole, and combinations thereof.

The polymer hydrogel of the invention can be administered to the subject in the form of a tablet or a capsule or other formulation suitable for oral administration. The tablet or capsule can further include one or more additional agents, such as a pH modifying agent, and/or a pharmaceutically acceptable carrier or excipient. The polymer hydrogel can also be administered as a component of a food or a beverage, such as is described in WO 2010/059725, incorporated herein by reference in its entirety.

In one embodiment, the present invention provides a pharmaceutical composition comprising a polymer hydrogel of the invention. The pharmaceutical composition can comprise the polymer hydrogel as an active agent, optionally in combination with a pharmaceutically acceptable excipient or carrier. For example, the pharmaceutical composition can be intended for oral administration to treat obesity, provide enhanced satiety, improve glycemic control, treat or prevent diabetes or aid in weight management. In another embodiment, the pharmaceutical composition comprises the polymer hydrogel in combination with another active agent. The polymer hydrogel can serve as a matrix, for example, for sustained release of the active agent.

The scope of the present invention includes the use of the polymer hydrogels obtainable by the method of the invention as an absorbent material in products which are capable of absorbing water and/or aqueous solutions and/or which are capable of media uptake when brought into contact with water and/or an aqueous solution. The polymer hydrogels of the present invention may be used as absorbent materials in the following fields, which are provided as non-limiting examples: dietary supplements (for example, as the bulking agents in dietary supplements for hypocaloric diets capable of conferring a sensation of lasting satiety being retained into the stomach for a limited period of time, or as water and low molecular weight compounds supplements, such as mineral salts or vitamins, to be included into drinks in a dry or swollen form); in agricultural products, for example, in devices for the controlled release of water and/or nutrients and/or phytochemicals, particularly for cultivation in arid, deserted areas and in all cases where it is not possible to carry out frequent irrigation; such products, mixed in a dry form with the soil in the areas surrounding the plant roots, absorb water during irrigation and are capable of retaining it, releasing it slowly in certain cases, together with the nutrients and phytochemicals useful for cultivation; in personal hygiene and household absorbent products, such as, for example, as the absorbent core in diapers, sanitary napkins and the like; in toys and devices, such as for example in products which are capable of significantly changing their size once brought into contact with water or an aqueous solution; in the biomedical field, for example, in biomedical and/or medical devices such as absorbent dressings for the treatment of highly exudative wounds, such as ulcers and/or burns, or in slow-release polymeric films suitable to slowly release liquids adapted for use in ophthalmology; in the body fluid management field, for example, for controlling the amount of liquids in an organism, for example in products capable of promoting the elimination of fluids from the body, such as, for example, in the case of edema, CHF (congestive heart failure), dialysis; and in home cleaning products.

The above-mentioned products, containing a polymer hydrogel of the present invention as the absorbent material, also fall within the scope of the invention.

The invention further includes the use of any of the polymer hydrogels of the invention in medicine. Such use includes the use of a polymer hydrogel in the preparation of a medicament for the treatment of obesity or any medical disorder or disease in which calorie restriction has a therapeutic, palliative or prophylactic benefit.

EXEMPLIFICATION

Example 1 Preparation of Citric Acid Cross-Linked Carboxymethylcellulose

Materials

| | |
|---|---|
| NaCMC | E&V, catalog number 72537 - 7H3SXF |
| Citric Acid | Sigma, catalog number 43309268 |
| Purified water | Chimica D'Agostino (Bari - Italy) |

Method

Purified water (10 kg) was added to a 10 liter Hobart mixer and agitated at 30 rpm. Citric acid (1.8 g) was added to the water and dissolved. NaCMC (600 g) was then added to the solution and the resulting mixture was agitated at room temperature at 60 rpm for 90 minutes and then at 30 rpm for 15 hours. The resulting solution was added to 10 stainless steel trays (1.030 kg solution per tray). The trays were placed in a Salvis Thermocenter TC240 oven at 45° C. for 24 hours. The trays were removed from the oven, the contents were inverted and the trays were placed back in the oven and maintained at 45° C. for 30 hours. After the desiccation the material was ground by means of a cutting mill (Retsch cutting mill) equipped with a 1 mm screen. The granulated material was then spread on the trays and cross-linked in the Salvis Thermocenter TC240 oven at 120° C. for 4 hours. The cross-linked polymer hydrogel thus obtained was washed with purified water for 24 hours to remove the unreacted reagents (by changing the washing solution 4 times). The washing stage allows the media uptake of the cross-linked polymer by increasing the relaxation of the network thus increasing the media uptake capacity of the final material obtained after a further desiccation step. After the washing the material was placed on trays and into the oven at 45° C. to dry. The dry material was then ground and sieved to a particle size from 0.1 mm to 1 mm.

Media Uptake Ratio (MUR)

For this example, equilibrium media uptake measurements for all the samples were carried out in a mixture of simulated gastric fluid (SGF) and water (1:8 v/v) using a Sartorius microbalance ($10^{-5}$ sensitivity). The media uptake ratio was measured by weighing samples (sieved between 400 μm and 600 μm) before and after their immersion in the SGF/water (1:8).

The results indicated that the media uptake ratio (MUR) of the sample increases with the time and reaches its maximum value after 30 minutes. The media uptake ratio for each tested sample is presented in Table 1 below.

TABLE 1

| time (h) | MUR (g/g) |
|---|---|
| 0.25 | 21 |
| 0.5 | 37 |
| 0.75 | 58 |
| 1 | 67 |
| 2 | 69 |

Discussion

The data show dependence of the absorption capacity with time up to 30 min. No relevant differences are noted between the samples at 1 h and 2 h. This is a typical behavior exhibited by superabsorbent hydrogels and is due to the Donnan Effect. The presence of fixed charges on the polymeric backbone, typical of polyelectrolyte gels, leads to significant rapid swelling of the polymer in water. This behavior is due to a Donnan equilibrium established between gel and the external solution, whose ionic strength strongly affects the swelling degree. In this case, the polymer hydrogel can be considered as a semipermeable membrane that allows the water to enter in order to dilute the fixed charges linked to the polymer backbones. Since the charges are fixed and they cannot move in the opposite direction, more water is necessary to reach the equilibrium, thus allowing the swelling of the polymer hydrogel.

The data presented here and in Example 8 support the idea that a significant effect of washing is the removal of unreacted polymer from the hydrogel. Such unreacted polymer can serve as a molecular spacer during the cross-linking process, serving to increase the distance between cross-linking sites. It is also believed that washing stretches the cross-linked polymer network, increasing polymer mobility and absorption kinetics.

Example 2 Study of the Effect of Washing Procedure on the Properties of Citric Acid Cross-linked Carboxymethylcellulose The samples were prepared according to the procedure described in Example 1 with the exception of the washing procedure. In this preparation the sample was divided into 4 parts, each of which was washed with distilled water 1, 2, 3 or 4 times. The first 3 washes were performed for 3 hours and the last one for 14 hours. The yield of the process was calculated as follows:

$$Y\% = W_{hydrogel}/W_{cmc}$$

where the $W_{hydrogel}$ is the weight of dry material obtained after the process and $W_{cmc}$ is the weight of the carboxymethylcellulose in the starting mixture. The media uptake ratio of each washed sample was determined in SGF/water (1:8) and the results are set forth in Table 2.

TABLE 2

| Number of washings | Yield | MUR (g/g) |
|---|---|---|
| 0 | 91% | 17 |
| 1 | 81% | 32 |
| 2 | 69% | 35 |
| 3 | 62% | 36 |
| 4 | 59% | 69 |

Discussion

The results indicate that the media uptake ratio increases with the number of washes. This is due to a reduction of the degree of cross-linking. The hydrogel network includes both physical entanglements and chemical cross-links. Without being limited by theory, it is believed that physical entanglements are reduced by washing due to the electrostatic repulsion between the chains and to the increased mobility of these chains due to the increased volume of the hydrogel. As a direct consequence of this enhanced absorption capacity, the yield of the process decreases. This is believed to be due to the solubilization of unreacted carboxymethylcellulose during the washing which decreases the final weight of the product. The reduction in yield may also relate to losses from the additional manipulation of the material required by the additional washing steps.

Example 3 Effect of Cross-Linking Time on the Properties of Citric Acid Cross-Linked Carboxymethylcellulose Method Purified water (10 kg) was added to a 10 liter Hobart mixer and agitated at 30 rpm. Citric acid (1.8 g) was added to the water and dissolved. NaCMC (600 g) was then added to the solution and the resulting mixture was agitated at room temperature at 60 rpm for 90 minutes and then at 30 rpm for 15 hours. The resulting solution was added to 10 stainless steel trays (1.030 kg solution per tray). The trays were placed in a Salvis Thermocenter TC240 oven at 45° C. for 24 hours. The trays were removed from the oven, the contents were inverted and the trays were placed back in the oven and maintained at 45° C. for 30 hours. After drying, part of the material was ground by means of a cutting mill (Retsch cutting mill) equipped with 1 mm screen, and one sample was stored in sheet form for control purposes (sample C). The remaining material was then sieved and divided into 2 parts according to Table 3.

TABLE 3

| Sample | Particle size range (μm) |
|---|---|
| A | 500-1000 |
| B | 100-500 |
| C | Sheet (infinite particle) |

Samples A, B and C were each divided into three parts. These portions of samples A, B and C and were then spread on the tray and cross-linked in the Salvis Thermocenter TC240 oven at 120° C. for 2, 3 or 4 hours. The resulting cross-linked polymer hydrogel was washed with distilled water for 24 hours in order to remove the unreacted reagents (by changing the washing solution 4 times). After washing, the material was placed on trays into the oven at 45° C. until complete dessication. The dry material was then ground and sieved between 100 μm and 1000 μm particle size.

Discussion

The media uptake ratio of these samples in SGF/water (1:8) is presented in Table 4.

TABLE 4

| Sample | Cross-linking Time (h) | MUR (g/g) |
|---|---|---|
| A | 2 | 80 |
| A | 3 | 74 |
| A | 4 | 58 |
| B | 2 | 88 |
| B | 3 | 83 |
| B | 4 | 69 |
| C | 2 | 95 |
| C | 3 | 86 |
| C | 4 | 83 |

It is evident that media uptake capacity decreases with increasing cross-linking time. However, the main particle size is not the most dominant parameter affecting media uptake.

Example 4 Effect of Cross-Linking Particle Size on Properties of Citric Acid Cross-Linked Carboxymethylcellulose Method Purified water (10 kg) was added to a 10 liter Hobart mixer and agitated at 30 rpm. Citric acid (1.8 g) was added to the water and dissolved. NaCMC (600 g) was then added to the solution and the resulting mixture was agitated at room temperature at 60 rpm for 90 minutes and then at 30 rpm for 15 hours. The resulting solution was added to 10 stainless steel trays (1.030 kg solution per tray). The trays were placed in a Salvis Thermocenter TC240 oven at 45° C. for 24 hours. The trays were removed from the oven, the contents were inverted and the trays were placed back in the oven and maintained at 45° C. for 30 hours. After the desiccation part of the material was ground by means of a cutting mill (Retsch, cutting mill) equipped with 1 mm screen, and one small sample was stored in sheet form for control purposes (sample D). The ground material was then sieved and divided into 3 parts according to Table 5.

TABLE 5

| Sample ID | Particle size range (μm) |
| --- | --- |
| A | 1000-3000 |
| B | 500-1000 |
| C | 100-500 |
| D | Sheet (infinite particle) |

Samples A-D were then spread on the trays and cross-linked in the Salvis Thermocenter TC240 oven at 120° C. for 4 hours. The cross-linked polymer hydrogels thus obtained were washed for 24 hours with distilled water to remove the unreacted reagents (by changing the washing solution 4 times). After washing, the material was spread on the trays and placed in the oven at 45° C. to dry. The dry material was then ground and sieved to a particle size from 100 μm and 1000 μm.

Discussion

The media uptake ratio (MUR) of Samples A-D in SGF:water (1:8) is presented in Table 6.

TABLE 6

| Sample | Media Uptake Ratio (g/g) |
| --- | --- |
| A | 64 |
| B | 63 |
| C | 55 |
| D | 80 |

Samples A, B and C had negligible differences in media uptake (around 15% which can be attributed to experimental error). Sample D, the cross-linked sheet, demonstrated an increased media uptake capacity.

Conclusions

As demonstrated by the media uptake ratio which is directly related to the cross linking density/efficiency, the samples which were cross-linked as particles demonstrated greater cross-linking efficiency due to their homogeneity. The sheet had its top side cross linked while its back side was hardly cross-linked, resulting in greater media uptake (over 35%).

Example 5 Determination of Degree of Cross-Linking of Citric Acid Cross-Linked Carboxymethyl Cellulose Method:

A disc of swollen hydrogel is tested through a uniaxial-compressive load by means of rotational rheometer (ARES Rheometric Scientific) equipped with a parallel plate tool. The discs were prepared by soaking for 24 h a dry cross-linked sheet of material in distilled water. Then the swollen sheet is cut in round disks of 25 mm in diameter through a PE punch. The disk is placed on the parallel plates of the rheometer for the compressive test with a compressive rate of 0.001 mm/s. Assuming that there are no changes in the volume of the sample during the compression test, Flory derived a relationship between the compressive stress and the compressive deformation for the case of a swollen crosslinked polymer, based on the assumption of Gaussian statistics for an affine deformation (eq. 3).

Although this approach is oversimplified, due to the assumption of constant volume (actually some water is squeezed out of the swollen sample as a result of compression), it can be used to understand gel deformation ($\alpha=(1-l_0)/l_0$, were $l_0$ and $l$ are the highs of the starting sample before and after compression respectively) and behavior under uniaxial compression in the case of small deformations ($\alpha \rightarrow 1$) and can be used for the evaluation of the ratio $\upsilon_e/V_0$ and of $\rho_x$ (see eq. 3).

Figure 3:
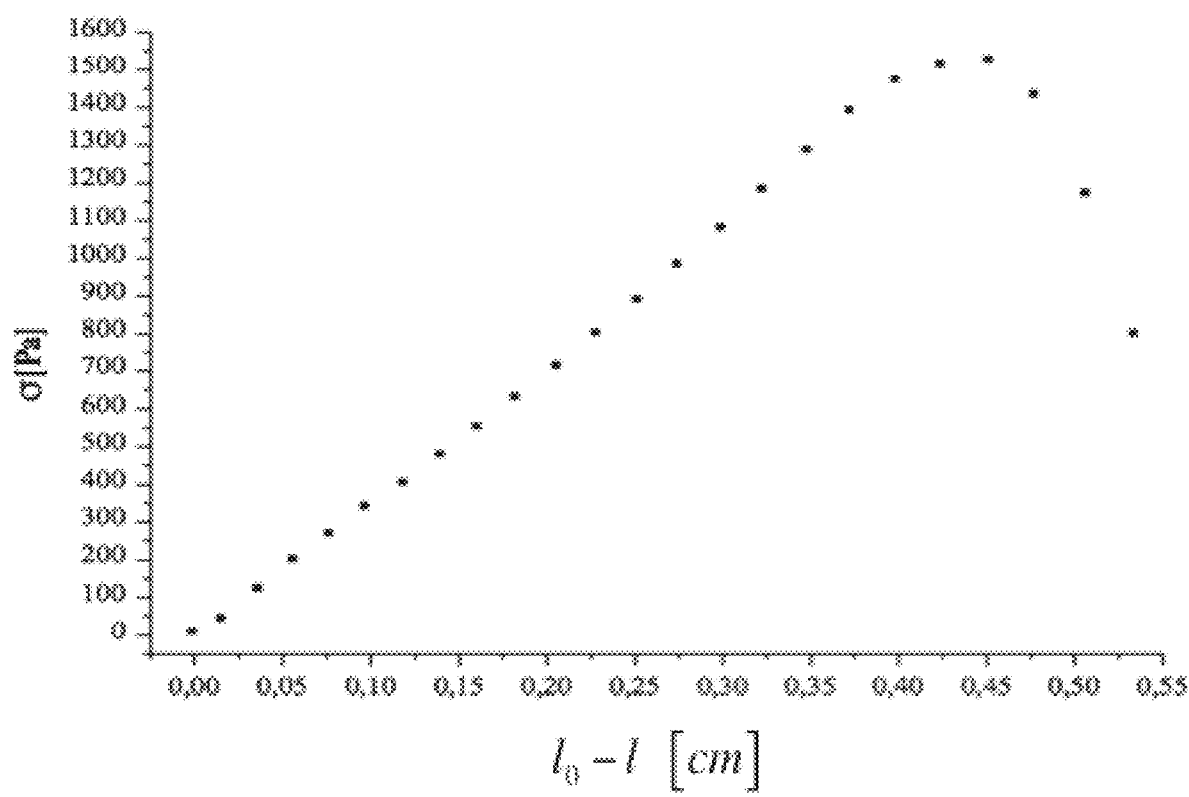
FIG. 3 is a plot of σ (Pa) versus $l_0-l$ (μ) from a typical compression experiment as described in Example 5.
Figure 4:
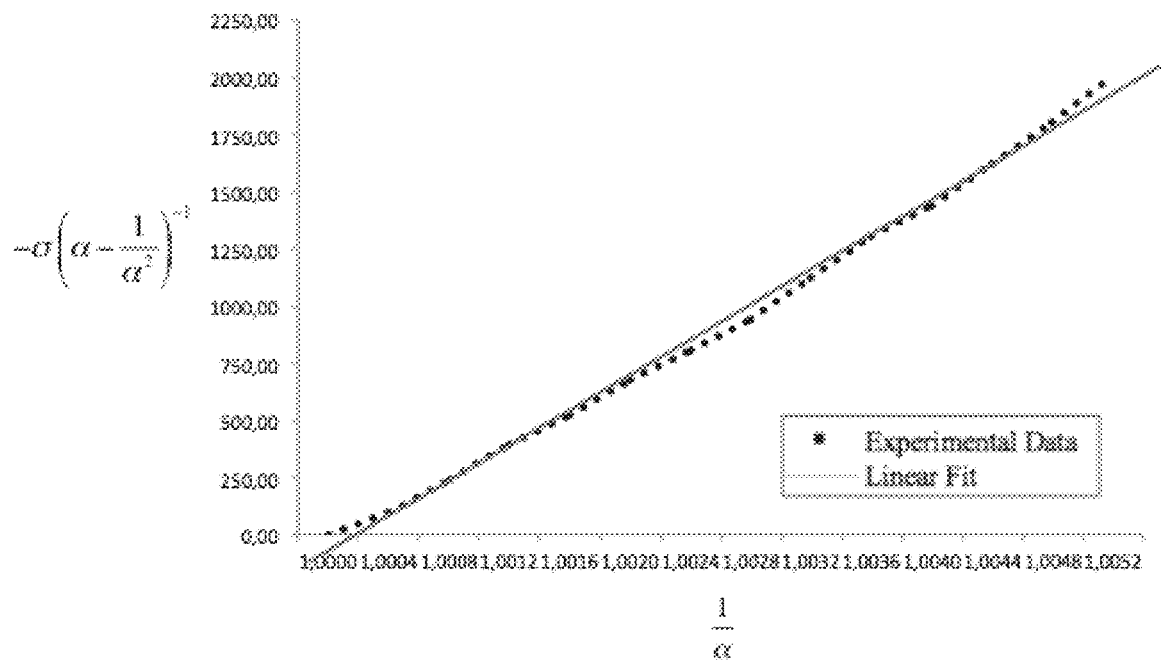
FIG. 4 is a plot of $-\sigma(\alpha-1/\alpha^2)^{-1}$ versus $1/\alpha$ from a typical compression experiment as described in Example 5.

The deviation from Gaussian statistics at large deformations can be taken into account by using a phenomenological expression to describe the behavior of a swollen crosslinked network submitted to uniaxial extension. This expression can be derived from the expression of Mooney-Rivlin strain energy function for swollen rubbers which accounts for both the deformation due to swelling and the deformation due to compression. Making the assumption of incompressibility, the following expression relating the uniaxial stress s (referred to the cross-sectional area of undeformed swollen sample) to the extension ratio, a, can be derived:

$$\sigma = 2\left(K_1 + \frac{K_2}{\alpha}\right)\left(\alpha - \frac{1}{\alpha^2}\right) \quad \text{(eq. 4)}$$

where σ has the same definition as in Eq. (3) and the values of $K_1$ and $K_2$ are proportional to the swelling ratio of the sample. According to Eq. (4), a plot of $\sigma(\alpha-1/\alpha^2)^{-1}$ vs $1/\alpha$ based on experimental data should be linear. A plot of σ (Pa) versus $l_0-l$ (μ) from a typical test is presented in FIG. 3. A plot of $-\sigma(\alpha-1/\alpha^2)^{-1}$ versus $1/\alpha$ from a typical experiment is set forth in FIG. 4.

Figure 5:
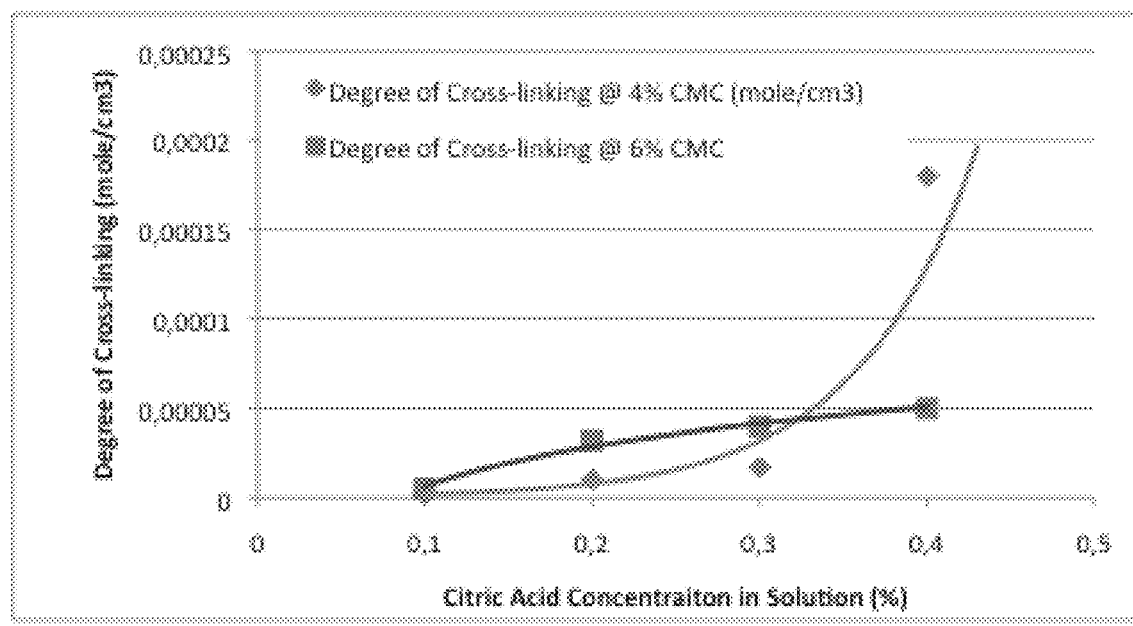
FIG. 5 is a graph showing the degree of cross-linking of citric acid cross-linked carboxymethylcellulose prepared with two different starting CMC concentrations as a function of citric acid concentration.

The slope of linear fit of the experimental data gives the value of G to be used in the eq. 3. Using this value, it is possible to evaluate the degree of crosslinking of the swollen hydrogel network. Measurements have been performed at different CMC concentrations and different amounts of citric acid, and results are reported in FIG. 5. Five samples were evaluated for each concentration and the plot in FIG. 5 is the average obtained excluding the both the higher and the lower value of the measurement obtained. The results show that the degree of crosslinking increases with increasing the citric acid concentration, which is in agreement with the assumption that the citric acid act as a chemical crosslinker for the polymer network, by means of a double anidrification/double esterification mechanism.

Figure 6:
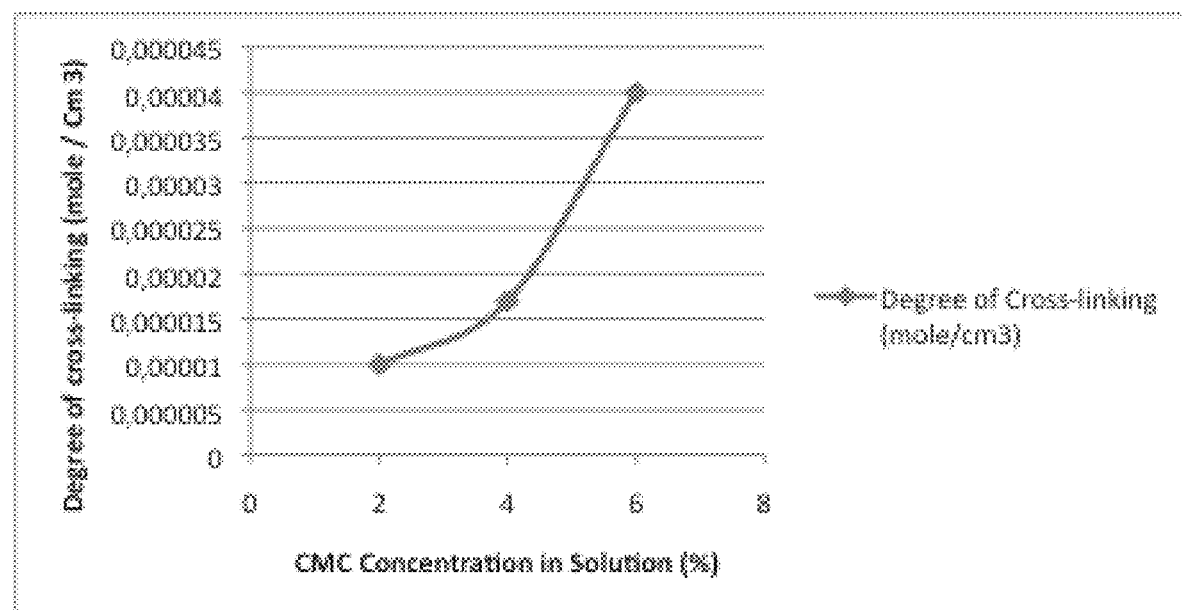
FIG. 6 is a graph showing the degree of cross-linking of citric acid cross-linked carboxymethylcellulose prepared with different starting CMC concentrations at 0.3% citric acid.

An evaluation of the degree of crosslinking have been also performed as a function of the polymer (CMC) concentration in the starting solution, as reported in FIG. 6, at a fixed citric acid concentration (0.3% wt/wt relative to CMC).

It can be observed that the degree of crosslinking increases by increasing the polymer concentration, at fixed crosslinker concentration, and this correlation is not linear. This occurs because the stabilization reaction occurs in a shrinked state, as described above. Thus, at increased concentration of polymer, the average distance between two adjacent polymer molecules is lower, and covalent bonds are created among molecules that potentially can be positioned at much higher distance once the polymer network is swollen, thus preventing the material to swell to its full potential, and increasing the effective degree of crosslinking, being the average distance between to subsequent crosslinking sites lower. The non linear correlation is thus explained as the variation of the average distance between polymer molecules is related to volumetric variation of the solid portion of the reactive mass.

Figure 7:
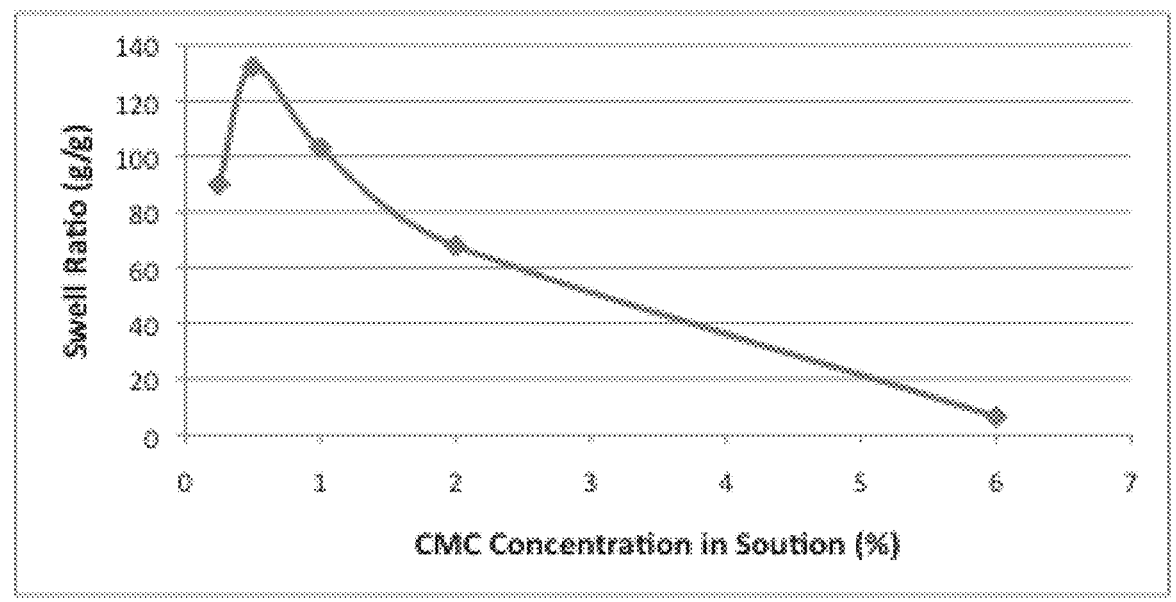
FIG. 7 is a graph showing the media uptake ratio in SGF/water 1:8 of carboxymethylcellulose prepared with different starting CMC concentrations at 0.3% citric acid.

According to what is stated above, it is expected that the media uptake capacity of the hydrogel is dependent on the polymer (CMC) concentration in the starting solution. This is confirmed by the graph in FIG. 7, where the media uptake ratio of the hydrogel is reported as a function of the polymer concentration in the starting solution, at a fixed (0.3% of the polymer) concentration of the crosslinker (citric acid). The data set forth in FIG. 7 were obtained on the same samples used for the compression measurements. These disc-shaped samples were placed in deionized water for 24 hours and then dried at 45° C. for 48 hours. The media uptake ratio was calculated using the weight before and after drying.

Table 7 compares properties of the material of this example prepared at a citric acid concentration of 0.3% by weight relative to carboxymethylcellulose and material prepared as described in Example 10.

TABLE 7

| SAMPLE | MUR in SGF/Water 1:8 | G' at 10 rad/s [Pa] | G" at 10 rad/s [Pa] | η at 0.5 rad/s [Pa*s] |
| --- | --- | --- | --- | --- |
| Example 5 | 27.46 | 4361.50 | 1877.5 | 905.00 |
| Prepared according to Example 10 | 72.15 | 1093.53 | 153.38 | 319.99 |

It is observed that, except for the very low concentration of 0.25% of CMC in the starting solution, where fully chemical stabilization of the polymer network is not expected, the media uptake ratio decreases with the amount of CMC. This reduction is due to an increased value of the elastic component due to an higher value of the degree of crosslinking. This suggests a proper correlation of the CMC concentration used during the synthesis as a function of the crosslinker concentration, with the aim to find a range of values of the reactants concentration able to provide a superabsorbent behaviour of the polymer in conditions closest to the actual use of the material (water, water solutions, gastro-intestinal fluids, etc.).

Example 6 Comparison of Structural Properties of Hydrogels Prepared Using Different Methods In this example, properties of hydrogels prepared using the methods of the invention were compared with those of hydrogels prepared as set forth in WO 01/87365 example IX, samples 202 and 203.

Preparation of Samples A and B
Materials: Sodium carboxymethyl cellulose—Aqualon 7HOF, pharmaceutical grade
Citric Acid—Carlo Erba, USP grade Samples A and B were prepared as described for samples 202 and 203 of Example IX of WO 01/87365. For both samples, a solution of 2% (w/w water) sodium carboxymethyl cellulose and citric acid (0.6% (w/w CMC) for Sample A; 1.0% (w/w CMC) for Sample B) was prepared in water by mixing until complete dissolution occurred. The solutions were poured into polypropylene trays and maintained at 95° C. for 16 hours. Thereafter, the dry sheets were ground using a Quadro Model U5 CoMill and the resulting powder was sieved. The fraction between 100 and 1000 µm was collected.

Preparation of Sample C
Materials: Sodium carboxymethyl cellulose—Aqualon 7H3SXF, pharmaceutical grade
Citric Acid—Carlo Erba, USP grade An aqueous solution of 6% (w/w water) sodium carboxymethyl cellulose and citric acid (0.3% w/w CMC) was prepared and mixed for 12 hours. The solution was then poured into a polypropylene tray and maintained at 45° C. for 12 hours. The residue was ground with a mill to provide a fine powder with a particle size distribution of 100-1000 µm. The powder was maintained at 120° C. for 5 hours, and then washed three times with deionized water at a water:powder ratio of 80:1 (v/v) with constant mixing. The powder was then dried for 48 h at 45° C. Thereafter, the dry material was round again using a Quadro Model U5 CoMill and the powder was sieved and the fraction between 100 and 1000 µm was collected.

Preparation of Sample D
Materials: Sodium carboxymethyl cellulose—Aqualon $7H_3SXF$, pharmaceutical grade
Citric Acid—Carlo Erba, USP grade
Sorbitol (ADEA Srl—food grade)

An aqueous solution of 2% (w/w water) sodium carboxymethyl cellulose, sorbitol (4% wt/wt water) and citric acid (1% w/w CMC) was prepared and mixed for 12 hours. The solution was then poured into a polypropylene tray and maintained at 45° C. for 48 hours. The residue was maintained at 80° C. for 12 hours, and then ground and washed three times with deionized water at a water: powder ratio of 80:1 (v/v) with constant mixing. The powder was then dried for 48 h at 45° C. The material was poured into a glass beaker with acetone for 3 desiccation steps of 2 hours each: 1/1, 1/1, 1/10 material to acetone ratio for each step respectively. Thereafter, the dry material was ground again using a Quadro Model U5 CoMill. The powder was sieved and the fraction between 100 and 1000 um was collected.

Characterization of Hydrogels
NMR Analysis

Approximately 0.02 g of each hydrogel sample was transferred into a glass vial and $D_2O$ (2 mL) at room temperature. The swollen hydrogels were allowed to stand for at least 24 h before being transferred to the NMR rotor (vide ultra).

HR-MAS NMR $^1H$ NMR spectra of hydrogel systems were recorded on a Bruker Avance spectrometer operating at 500 MHz proton frequency, equipped with a dual $^1H/^{13}C$ HR MAS (High Resolution Magic Angle Spinning) probe-head for semi-solid samples (Lippens, G. et al., M. Curr. Org. Chem. 1999, 3, 147). The basic principle of this approach can be summarized as follows. The fast rotation of the sample at the so called magic-angle (54.7° with respect to the z-direction of the stray field of the NMR magnet) averages the dipole-dipole interactions and susceptibility distortions, causing a dramatic improvement of spectral resolution (Viel, S.; Ziarelli, F.; Caldarelli, S., *Proc. Natl. Acad. Sci. U.S.A.* 2003, 100, 9696). The hydrogels prepared as described above were transferred into a 4 mm $ZrO_2$ rotor containing a volume of about 50 µL. All of the $^1H$ spectra were acquired with a spinning rate of 4 kHz to eliminate the dipolar contribution.

T2 filtration was achieved by using the classic Carr-Purcell-Meiboom-Gill spin-echo pulse sequence with 1 ms echo-time.

The water self-diffusion coefficient was measured by Diffusion Ordered correlation SpectroscopY (DOSY) experiments, based on the pulsed field gradient spin-echo (PGSE) approach. A pulsed gradient unit capable of producing magnetic field pulse gradients in the z-direction up to 53 $G·cm^{-1}$ was used.

HRMAS-NMR: Pulse-Collect with Water Presaturation

Figure 8:
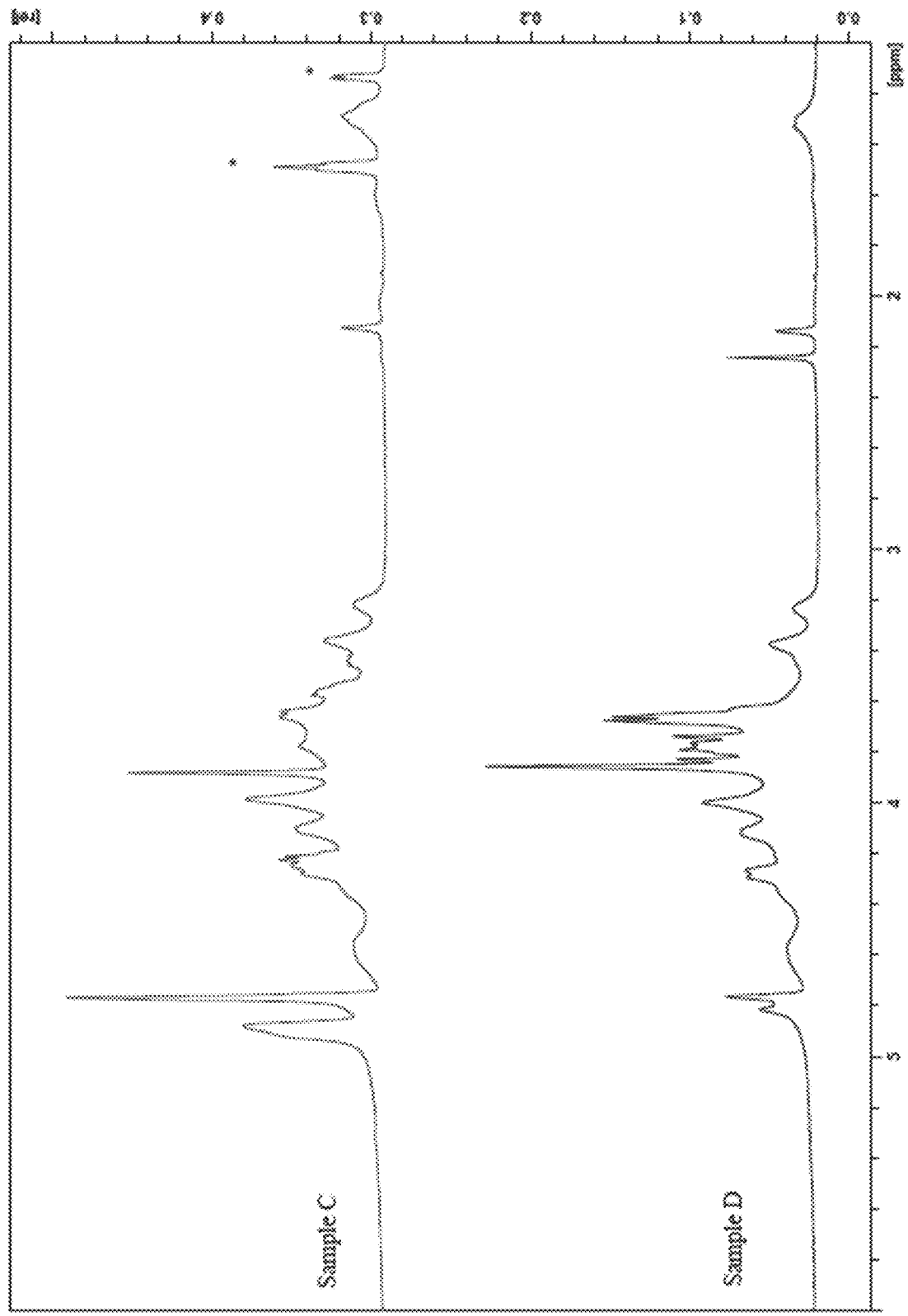
FIG. 8 presents the HRMAS NMR spectra of samples C and D of Example 6.
Figure 9:
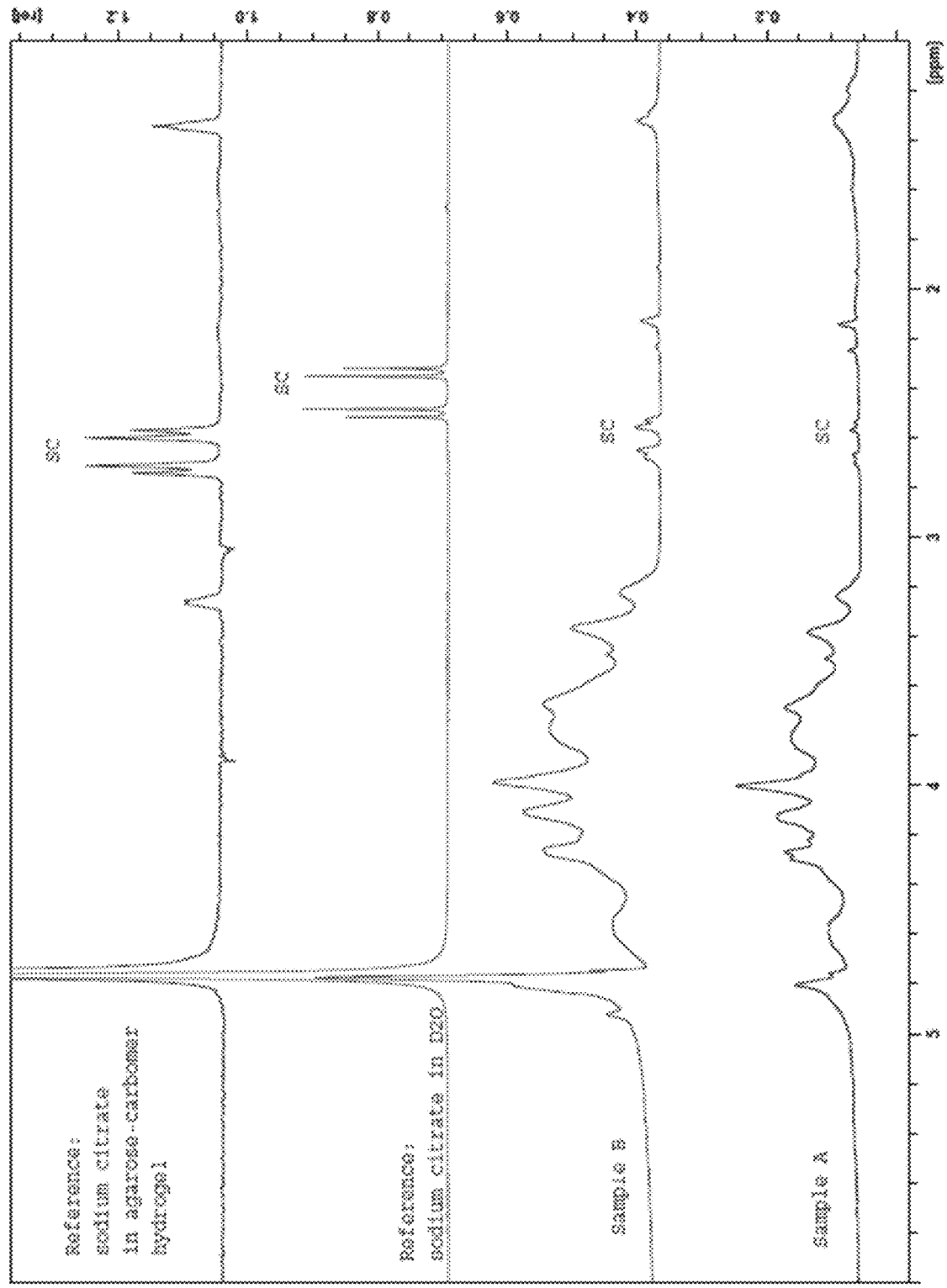
FIG. 9 presents the HRMAS NMR spectra of samples A and B of Example 6.

The spectra of the hydrogel samples C and D are shown in FIG. 8. The corresponding spectra of samples A and B are set forth in FIG. 9. The spectra were acquired by using the presaturation of the intense signal due to the residual water 4.76 ppm. The spectra represent a fingerprint of the polymeric gel. The peaks labelled with * disappeared after some days. They can thus be due to some metastable state evolving to equilibrium with time. A striking feature characterize these samples. In the spectra of samples A and B, the AB quartet of sodium citrate, indicated in the spectra as "SC", is present. This means these hydrogels have a quantity of free sodium citrate. In order to double-check the assignment, the spectra of pure sodium citrate in a reference standard hydrogel preparation (agarose-carbomer) and in $D_2O$ solution are also shown (first and second traces from top, respectively). It is important to stress that the signal of free citrate is not present in samples C and D (vide ultra).

HRMAS-NMR: T2 Filtering

In the general case of cross-linked, swellable polymers, the acquisition of the NMR signal after T2 filtration allows the extraction of magnetization arising from:
  a. the low molecular weight fractions of a polydisperse polymer;
  b. The part of the backbone of the polymer with higher mobility;
  c. any dangling chains or groups with faster motion than the backbone; and
  d. any small molecule absorbed, adsorbed, entrapped or encapsulated within the polymeric matrix.

For samples A, B and C, the spectral signals which survive after T2 filtration are likely due to factors b and d.

Figure 10:
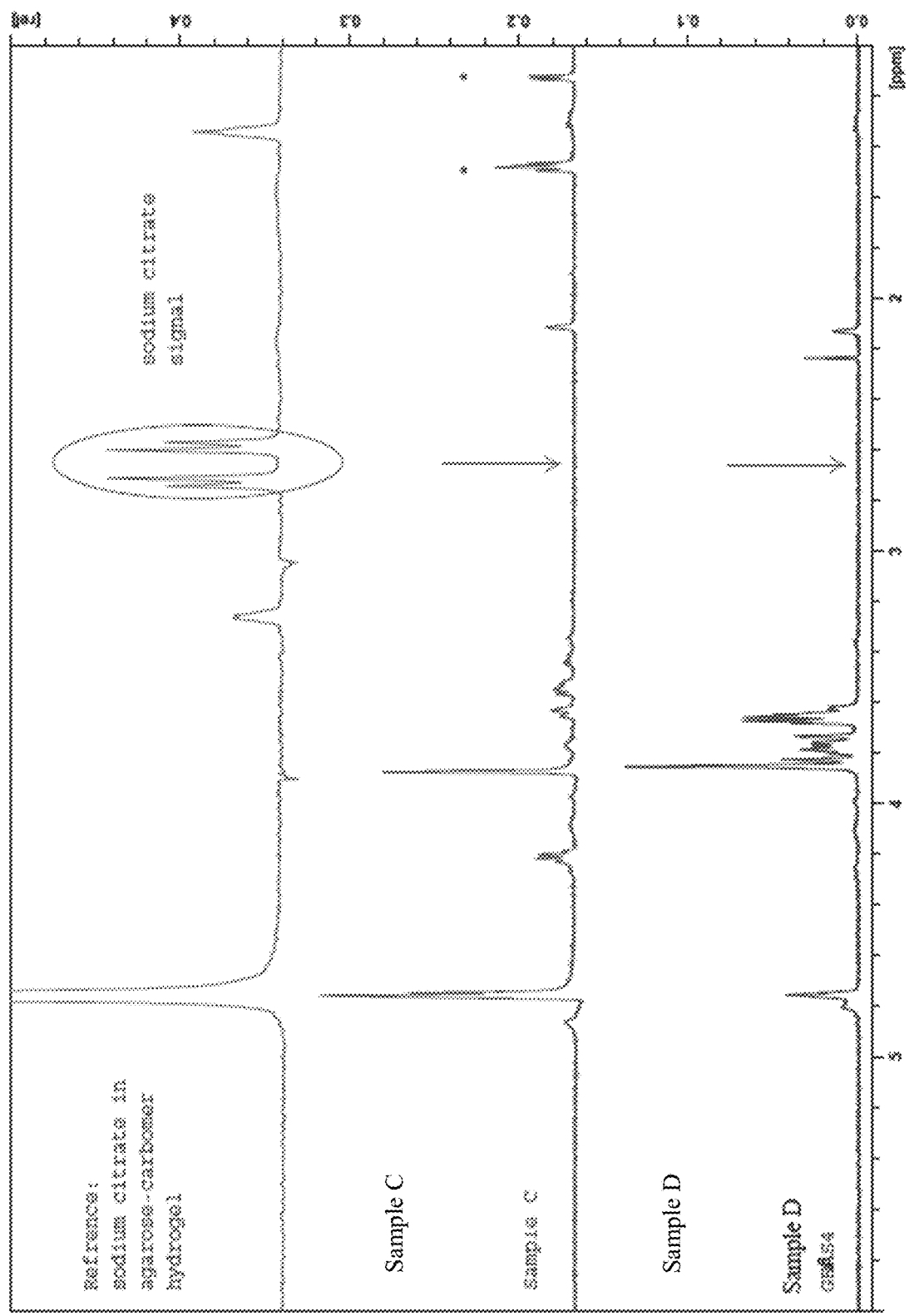
FIG. 10 presents the HRMAS NMR spectrum of samples C and D of Example 6 with T2 filtering.

FIG. 10 shows the superimposition of the spectra of samples C and D collected with T2 filtering. As a general comment, sample C shows some peaks that are probably due to metastable states. The peaks labelled with * indeed vanish after the sample is allowed to stand for 48 h. The spectrum of sample D shows sharp peaks in the spectral region of the glucose backbone, indicating similar chain dynamics. The interpretation of sample C is less clear, probably for the reasons mentioned above. T2 filtered HRMAS NMR spectra confirm that samples C and D do not contain free citrate. The signal due to sodium citrate in the reference gel is shown in the top trace of FIG. 10 (oval frame). The arrows indicate where in the spectra of these samples such signals would be if present.

Figure 11:
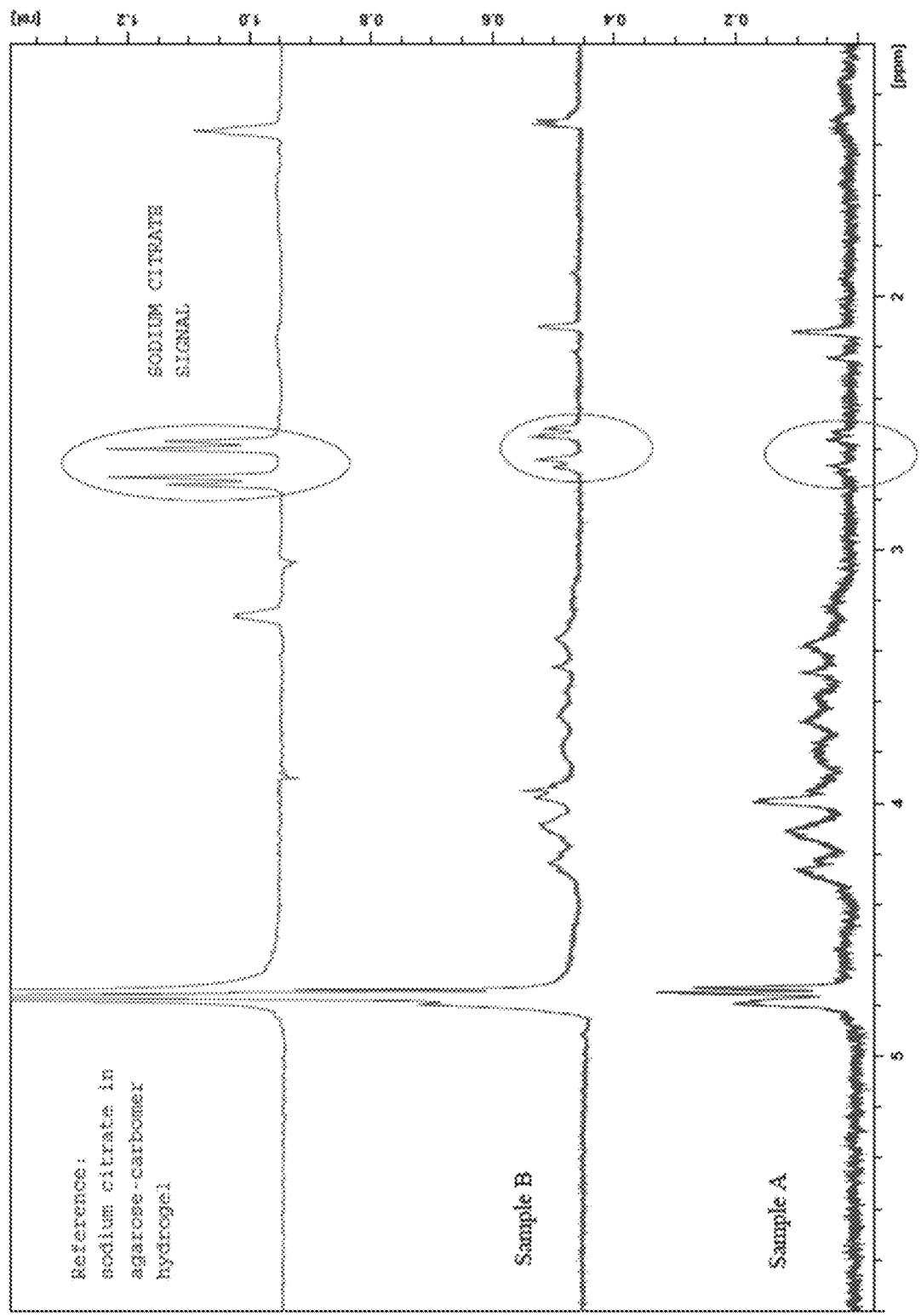
FIG. 11 presents the HRMAS NMR spectrum of samples A and B of Example 6 with T2 filtering.

The results for samples A and B are shown in FIG. 10. The signal is, in general, less abundant than that observed in samples C and D, indicating a slower chain dynamics. Differently from what observed in samples C and D, samples A and B do contain detectable amounts of free citrate. The corresponding NMR signals are in oval frames in FIG. 11.

DOSY HRMAS-NMR

The self-diffusion coefficient D of the water molecules inside the hydrogels was also measured. In some cases water molecules may interact strongly with the polymeric matrix, thus giving rise to different types of water according to the transport behavior: bulk water and bound water. If the two types of water are in fast exchange on the NMR time-scale, the observed D is the population-weighted average of Dbound and Dbulk, whereas if the bound and free water are in slow exchange on the NMR timescale, two different NMR signals are observed and the Dbound and Dbulk coefficients can be measured (Mele, A.; Castiglione, F. et al *J. Incl. Phenom. Macrocyc. Chem.,* 2011, 69, 403-409).

In the present study, the experimental D measured for each sample falls in the range 2.3 to $2.6 \times 10^{-9}$ $m^2\ s^{-1}$. In view of the uncertainty associated with the measurement, it can be concluded that the water inside the hydrogels shows a self-diffusion coefficient in good agreement with that of bulk water reported in the literature at the same temperature (Holz, M.; Heil, S. R.; Sacco, A. Phys. Chem. Chem. Phys., 2000, 2, 4740-4742). Therefore, no specific water/polymer interactions can be accounted for in these systems.

Conclusions

HRMAS-NMR methods are suitable for a fingerprint characterization of hydrogels made of citric acid cross-linked CMC polymeric hydrogels. Sample C does not show detectable traces of free citric acid/citrate, whereas samples A and B clearly and unambiguously show the NMR signal of citrate. This confirms that in samples A and B the double anhydrification/double esterification reaction is inhibited by the presence of water during the crosslinking stage of these samples, which is associated with the absence of the desiccation and grinding steps before crosslinking.

Sample C shows faster chain dynamics compared to samples A and B. This is a consequence of the absence of any washing and further desiccation steps in the synthesis of these samples. This is related to the observed faster absorption of water by sample C.

Water molecules inside the polymeric matrices show transport properties close to free, bulk water, thus indicating that no specific interactions of the water molecules with the polymer are present in these hydrogels.

The data suggest that samples A and B are physically crosslinked in a stable, compact network compared to the chemically stabilized, low crosslinked and highly mobile network structure of sample C. As shown below, this results in higher swelling capacity and faster swelling kinetics of sample C compared to samples A and B.

Swelling Kinetics

Each of the samples provided a uniform, transparent, highly viscous hydrogel upon treatment with deuterated water, as described above. Both samples B and C showed a decreased capability to absorb water compared to sample A (0.02 g of samples/1 mL water).

During the sample preparation, a different swelling behavior of sample C compared to samples A and B was observed. Sample C provided a dense, viscous hydrogel almost immediately after the addition of water, whereas samples A and B required much longer time to reach a single phase, homogeneous gel state.

Equilibrium Swelling

Media uptake measurements were performed on samples in the powder form (100-1000 microns particle size distribution) soaked for 30 minutes in different media (DI water, NaCl 0.9%, SGF/water 1:8). SGF is a Simulated Gastric Fluid. One liter of SGF is obtained by mixing 7 ml HCl 37% with 2 g NaCl and 993 ml of water. After NaCl dissolution 3.2 g of pepsin are added. Results for three aliquots of each sample are reported in Tables 8-10.

TABLE 8

| | Sample A | | |
|---|---|---|---|
| | Media uptake ratio in deionized water | Media uptake ratio in 9% NaCl | Media uptake ratio in SGF/Water 1:8 |
| 1 | 39.35 | 21.51 | 30.3 |
| 2 | 44.84 | 20.66 | 32 |
| 3 | 41.66 | 23.33 | 30.7 |
| Average | 41.95 | 21.83 | 31.00 |

TABLE 9

| | Sample B | | |
|---|---|---|---|
| | Media uptake ratio, deionized water | Media uptake ratio, 9% NaCl | Media uptake ratio, SGF/Water 1:8 |
| 1 | 23.41 | 14.6 | 21.6 |
| 2 | 23.35 | 15.09 | 20.65 |
| 3 | 23.25 | 15.53 | 23.6 |
| Average | 23.34 | 15.07 | 21.95 |

TABLE 10

| | Sample C | | |
|---|---|---|---|
| | Media uptake ratio, deionized water | Media uptake ratio, 9% NaCl | Media uptake ratio, SGF/Water 1:8 |
| 1 | 133.9 | 57.2 | 70 |
| 2 | 142.23 | 54.81 | 72.54 |
| 3 | 139.24 | 58.92 | 73.91 |
| Average | 138.46 | 56.98 | 72.15 |

The media uptake ratio in all three media is significantly greater for sample C than for samples A and B. This is due to the differences in molecular structure discussed in the previous chapter, and in particular to the difference in the mechanism of stabilization of the macromolecular network and the increased mobility of the macromolecular moieties. These properties are in turn associated with the different synthesis processes used for these samples and, in particular, the desiccation, grinding, washing and second drying processes included in the synthesis of sample C.

Mechanical Properties

The storage modulus (G'), the loss modulus (G") and the viscosity of the samples were evaluated after soaking three aliquots of each sample in SGF/water 1:8 for 30 minutes. A rheometer equipped with parallel plates (25 mm diameter) was used for the analyses. The frequency range was fixed between 1 rad/s to 50 rad/s and the strain was fixed at 0.5% (value in which the parameters present a linear behavior in a strain sweep test: fixed frequency at 1 Hz and variable strain). The values (G'-G"-viscosity) were registered at 10 rad/s. The results for samples A, B and C are set forth in Tables 11-13, respectively.

TABLE 11

| | Sample A | | |
|---|---|---|---|
| | G' at 10 rad/s [Pa] | G" at 10 rad/s [Pa] | η at 0.5 rad/s [Pa*s] |
| 1 | 3252.83 | 704.47 | 279.68 |
| 2 | 2371.82 | 551.42 | 271.76 |
| 3 | 2585.11 | 594.41 | 283.98 |
| Average | 2736.59 | 616.77 | 278.47 |

TABLE 12

| | Sample B | | |
|---|---|---|---|
| | G' at 10 rad/s [Pa] | G" at 10 rad/s [Pa] | η at 0.5 rad/s [Pa*s] |
| 1 | 4055.94 | 998.83 | 320.17 |
| 2 | 4425.04 | 1004.82 | 287.41 |
| 3 | 2654.34 | 702.95 | 279.89 |
| Average | 3711.77 | 902.20 | 295.82 |

TABLE 13

| | Sample C | | |
|---|---|---|---|
| | G' at 10 rad/s [Pa] | G" at 10 rad/s [Pa] | η at 0.5 rad/s [Pa*s] |
| 1 | 1176.55 | 158.67 | 337.28 |
| 2 | 1100 | 156.88 | 322.89 |
| 3 | 1004.05 | 144.58 | 299.81 |
| Average | 1093.53 | 153.38 | 319.99 |

Larger values of both conservative (G') and dissipative (G") moduli are in accordance with the lower swelling capacity of samples A and B. Due to absence of a washing step following cross-linking, a more compact, highly entangled and strongly stabilized structure with secondary bonding is expected for these samples compared to sample C. This results in a larger chemical constraint and, in turn, to a lower swelling capacity of samples A and B. The lower chemical mobility associated with the different structure of these samples is also responsible for their greater mechanical properties.

Conclusions

Differences in synthesis procedures between samples A and B and sample C result in different hydrogel properties. The primary differences relate to the absence of desiccation, grinding, washing and drying steps for samples A and B. Without being bound by theory, this is believed to result in inhibition of the double anhydrification/double esterification process, which requires the elimination of water from the reaction mixture, as water itself is a product of the reaction. This is also believed to result in a different stabilization mechanism for samples A and B compared to sample C and, in turn, different molecular structure and behavior.in terms of swelling kinetic, swelling capacity and mechanical properties.

Example 7 Large Scale Preparation of Hydrogels

Figure 12:
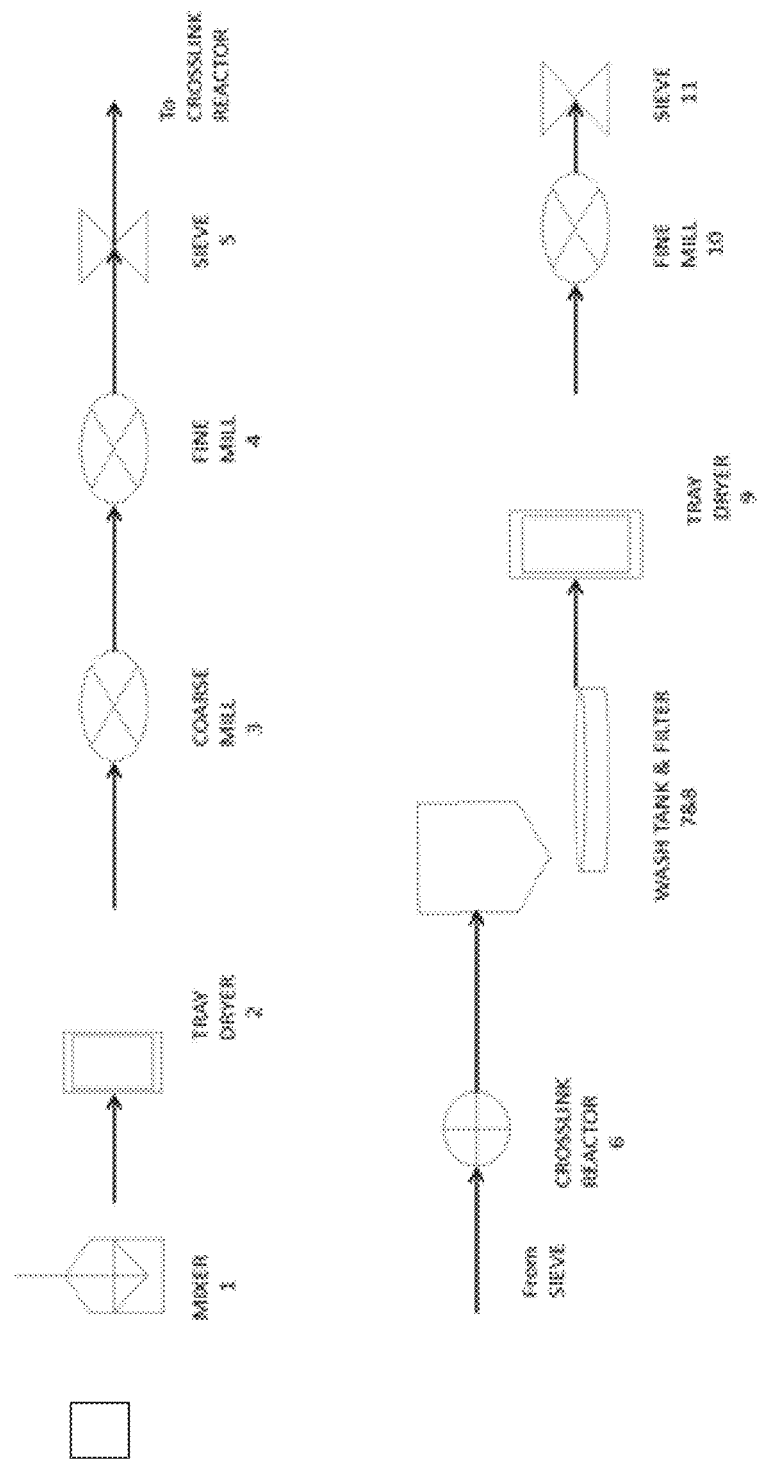
FIG. 12 is a schematic diagram illustrating apparatus useful for producing a polymer hydrogel.

A process for producing hydrogel particles on a multi-Kg scale is performed using the apparatus schematically depicted in FIG. 12. Sodium carboxymethylcellulose (6% wt/wt water), citric acid (0.3% wt/wt sodium carboxymethylcellulose) and water are mixed at room temperature and pressure in a low shear mixing vessel (mixer, 1) until a homogeneous solution is formed. The solution is transferred to trays so as to maintain a solution depth of about 30 mm. The trays are placed in an atmospheric forced air oven (tray dryer, 2), and dried for 16 to 24 hours at 85° C. The temperature is then lowered to 50° C. until drying is complete. The total drying time is about 60 hours. The resulting residue is in the form of a sheet, which is ground using a coarse mill (3) and fine mill (4) and sieved (sieve, 5) to provide a sample comprising particles of size between 100 and 1600 μm. The particles are placed in a crosslink reactor (6) and maintained at 120° C. and atmospheric pressure for 3 to 10 hours. The resulting hydrogel is transferred to a wash tank (7) and washed at ambient temperature and pressure with an amount of water between 150 and 300 times the polymer weight. The free water is removed from the hydrogel by filtration (Filter, 8). The hydrogel is placed on trays at a thickness of about 40 mm. The trays are placed in an atmospheric forced air oven (tray dryer, 9) and dried for 24-30 hours at 85° C. The temperature is then lowered to 50° C. until dry. The total drying time is about 60 hours. The dried material is ground into particles using a fine mill (10) and mechanically sieved (sieve, 11) to obtain particle fractions between 100 and 1000 μm.

Using this general process and starting with greater than 4 Kg of sodium carboxymethylcellulose, the yield was over 70% of powder with a particle size range between 100 and 1000 μm. The powdered hydrogel product met the product specifications as detailed in Table 14.

TABLE 14

Final Product Specifications

| Attribute | Specifications | Method |
| --- | --- | --- |
| Appearance | Yellowish to light brown glassy powder | Visual |
| Media uptake | NLT 50x reported as g/g | 1 g in 200 mL SGF/water 1:8 for 30 minutes |
| Particle size distribution | At least 95% of particles between 100 and 1000 μm | Estimation by analytical sieving |
| Tapped density | NLT 0.6 g/mL | Bulk density and tapped density of powders. |
| Elastic modulus | NLT 350 Pa | Analysis of swollen particles with parallel plate rheometer |
| Loss on drying | NMT 10% | Loss on drying at 100° C. for 20 minutes |
| Microbiology | Total Aerobic Microbial count NMT 1000 CFU/g Total Combined Yeasts/Molds NMT 100 CFU/g Absence of *E. coli* in 1 g | Microbiological examination of non-sterile products, microbial enumeration |

Example 8 Study of the Effect of Washing Procedure on the Properties of Citric Acid Cross-Linked Carboxymethylcellulose Hydrogel samples were prepared according to the procedure described in Example 7.

100 g dried hydrogel was mixed with 5000 g deionized water for 90 minutes. This wet slurry was passed though a large mesh stainless steel filter (500-1000 μm pore size). 2.31 Kg of wet hydrogel was collected. The filtrate was saved for future analysis. The wet gel was added again to 5000 g deionized water for additional 120 minutes. The material was filtered as before and 2.28 Kg of gel was collected. The filtrate was saved for future analysis.

The filtrate from the two washes was poured into glass drying pans and placed in a forced air oven overnight to dry at 105° C.

Results:
First Wash:
 Tare: 764.3 g
 Sample weight: 778.4 g
 Difference: 14.1 g
Second Wash:
 Tare: 764.3 g
 Sample weight: 764.4 g
 Difference: 0.1 g
Observations:

It is possible that some gel particles slipped through the filter, as a small number of particles were observed in the first filtrate sample upon drying. No gel particles were observed in dried residue of the second filtrate.

Conclusions

1) About 15% of the CMC does not react and is washed out of the gel.

2) In this experiment, 99.5% of the unreacted CMC is washed out after 90 minutes of washing.

Example 9 Effect of Citric Acid Concentration on Hydrogel Properties

Sodium carboxymethylcellulose was mixed in aqueous solution with citric acid at different concentrations. The mixture was dried in the oven (45° C.) and then ground to form 100 1000 μm particles. These particles were cross-linked at 120° C. for 4 hours. The elastic (Storage) modulus (G'), Loss Modulus (G"), viscosity (η), and media uptake in SGF/water 1:8 (recorded after 30 minutes) were determined for the gel particles.

The results are set forth in Table 15, which presents the NaCMC concentration by weight relative to the weight of water and the citric acid concentration by weight relative to the weight of NaCMC. MUR is the media uptake ratio in water:simulated gastric fluid 8:1.

TABLE 15

| NaCMC (wt/wt water) | CA (wt/wt CMC) | MUR | Particle size | G' (Pa) | G" (Pa) | Viscosity (Pa*s) |
| --- | --- | --- | --- | --- | --- | --- |
| 6% | 0.05% | 124.53 | 100-500 | 75 | 22 | 30 |
| 6% | 0.05% | 130.10 | 500-1000 | 79 | 22 | 26 |
| 6% | 0.1% | 67.83 | 100-500 | 1012 | 325 | 246 |
| 6% | 0.1% | 73.38 | 500-1000 | 1163 | 357 | 410 |
| 6% | 0.15% | 58.79 | 100-500 | 1524 | 447 | 279 |
| 6% | 0.15% | 61.40 | 500-1000 | 1612 | 432 | 536 |
| 6% | 0.2% | 40.52 | 100-500 | 3180 | 1083 | 388 |
| 6% | 0.2% | 40.24 | 500-1000 | 2231 | 704 | 534 |
| 6% | 0.25% | 33.56 | 100-500 | 3364 | 1456 | 567 |
| 6% | 0.25% | 34.12 | 500-1000 | 3289 | 1567 | 646 |
| 6% | 0.3% | 27.60 | 100-500 | 4456 | 1920 | 829 |
| 6% | 0.3% | 27.32 | 500-1000 | 4267 | 1835 | 981 |
| 6% | 0.4% | 20.12 | 100-500 | 6259 | 2517 | 1172 |
| 6% | 0.4% | 19.56 | 500-1000 | 5348 | 1932 | 1489 |

Figure 13:
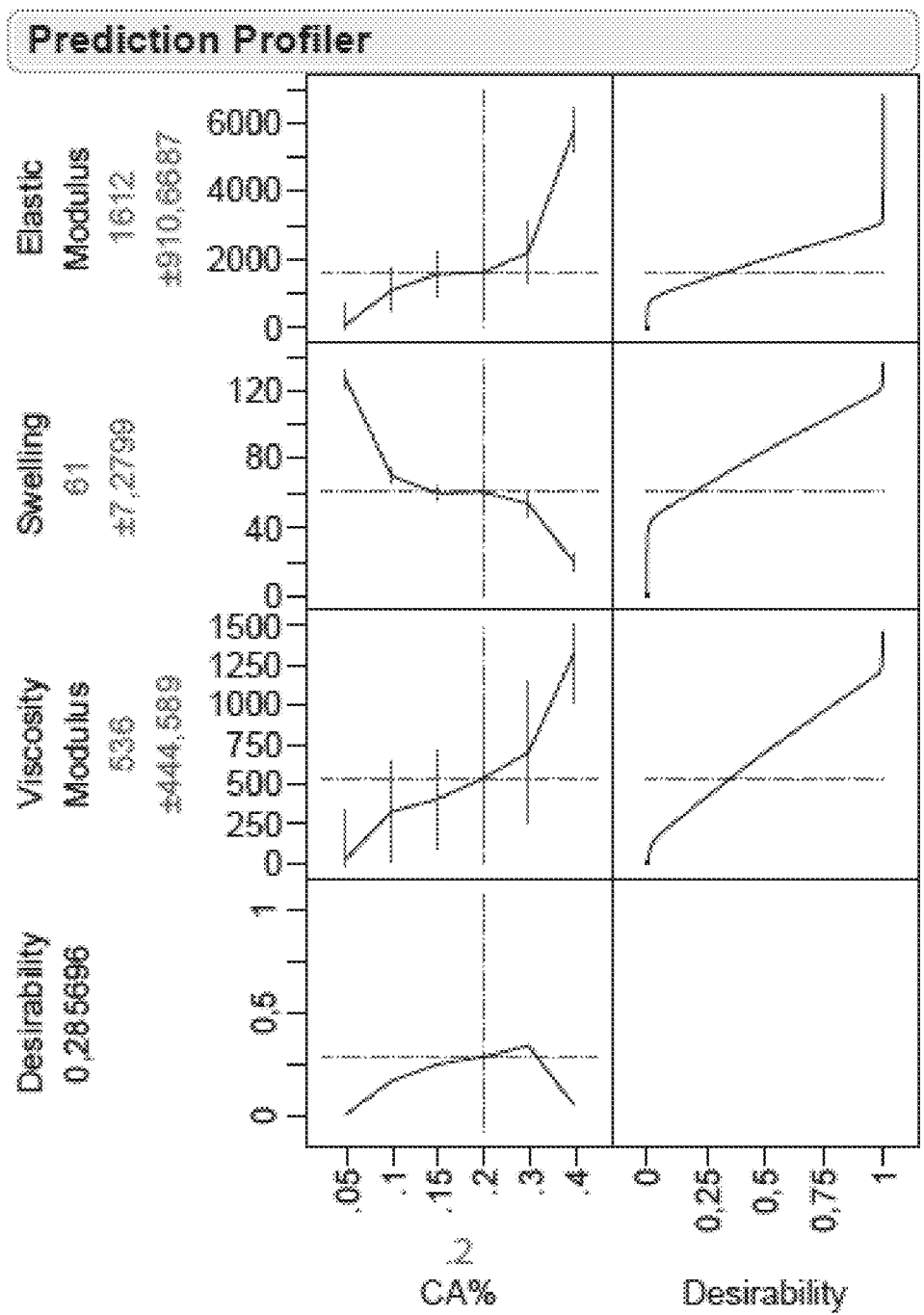
FIG. 13 presents graphs showing the predicted dependence of elastic modulus, swelling, viscosity modulus and desirability as a function of citric acid concentration as described in Example 9.

The above data were analyzed using an Experimental Design Software (IMP, by SAS Institute, Inc). The results are shown in FIG. 13, which shows that increasing citric acid concentration results in increasing elastic and viscosity moduli, but at the expense of swelling capacity. Desirability, which takes into account target ranges of eleastic modulus, viscosity modulus and swelling capacity, or media uptake ratio in SGF/water 1:8, is maximized at a citric acid concentration of 0.3% by weight relative to the weight of carboxymethylcellulose, with relatively little change from about 0.15% to about 0.35%.

Conclusions

The results show a strong relationship between the concentrations of NaCMC and citric acid. When optimized for human therapeutic benefits with elastic modulus similar to masticated food (1000-5000 Pa for unwashed particles and 350-1000 Pa for washed particles) the maximum media uptake was between citric acid concentrations from 0.15% to 0.3% at 6% NaCMC.

Example 10

To validate the results of Example 9, the study was repeated using 6% NaCMC with 0.3% CA. The hydrogel was prepared as described in Example 9 and then was washed three times in deionized water and then desiccated again. The results, which are set forth in Table 16, demonstrated good media uptake of over 70 in SGF/water 1:8 with an elastic modulus of greater than 1000 Pa. Table 17 presents the results of a study of the swelling kinetics of this material in SGF/water 1:8. The results demonstrate rapid swelling of the hydrogel in this medium.

TABLE 16

| MUR in DI water | MUR in 9% NaCl | MUR in SGF/Water 1:8 | G' at 10 rad/s [Pa] | G" at 10 rad/s [Pa] | η at 0.5 rad/s [Pa*s] |
|---|---|---|---|---|---|
| 138.46 | 50.99 | 72.15 | 1093.53 | 153.38 | 319.99 |

TABLE 17

| Media Uptake time | Media uptake ratio SGF/Water 1:8 (relative to value at 30 min.) |
|---|---|
| 5 min | 53% |
| 10 min | 79% |
| 15 min | 91% |
| 20 min | 94% |
| 30 min | 100% |

Example 11

Hydrogels of citric acid-cross-linked carboxymethylcellulose were prepared as generally described in WO 2009/021701. Aqueous solutions of 2% sodium carboxymethylcellulose (wt/wt water), 1% citric acid (wt/wt carboxymethylcellulose) and either no sorbitol or 4% sorbitol (wt/wt carboxymethylcellulose) were agitated, the solution was poured into a pan, dried at 30° C. for 24 hours and then maintained at 80° C. for 24 hours. The resulting hydrogels were washed and dried in acetone, as described in WO 2009/021701.

The properties of the hydrogel prepared with 4% sorbitol are set forth in Table 18. The properties of the hydrogel prepared in the absence of sorbitol could not be determined because this hydrogel dissolved in water during the washing step.

TABLE 18

| Swelling ratio in Demineralized water | Swelling ratio in NaCl | Swelling ratio in SGF/Water 1:8 | G' at 10 rad/s [Pa] | G" at 10 rad/s [Pa] | η at 10 rad/s [Pa*s] |
|---|---|---|---|---|---|
| 169.91 | 50.99 | 59.32 | 2219.37 | 266.74 | 517.10 |

These results demonstrate that at low concentrations of carboxymethylcellulose, for example 2% (wt/wt water), production of a stabilize hydrogel requires a physical spacer, such as sorbitol, a higher concentration of citric acid and/or a higher cross-linking temperature. It is believed that sorbitol acts as a plasticizer for the carboxymethylcellulose, increasing chain mobility and thereby reducing the energy required for cross-linking.

Example 12

Hydrogels were prepared as described in Example 9 at carboxymethylcellulose concentrations of 2 to 6% by weight relative to water and a citric acid concentration of 0.1% by weight relative to caboxymethylcellulose. The cross-linking time was either 4 hours or six hours. The hydrogel products were not washed. The hydrogels were characterized by media uptake in SGF/water 1:8, G', G" and η. The results are set forth in Tables 19 and 20.

TABLE 19

| NaCMC (%) | CA (%) | Time | MUR | G' | G" | η |
|---|---|---|---|---|---|---|
| 2 | 0.1 | 4 | NA | NA | NA | NA |
| 4 | 0.1 | 4 | NA | NA | NA | NA |
| 6 | 0.1 | 4 | 51 | 1738 | 171 | 144 |
| 6 | 0.1 | 4 | 47 | 2171 | 228 | 313 |

TABLE 20

| NaCMC (%) | CA (%) | Time | MUR | G' | G" | η |
|---|---|---|---|---|---|---|
| 2 | 0.1 | 6 | 38 | 2501 | 390 | 290 |
| 4 | 0.1 | 6 | 47 | 2283 | 246 | 497 |
| 6 | 0.1 | 6 | 39 | 2461 | 291 | 302 |

The results demonstrate that at low concentrations of citric acid a longer cross-linking time is needed. Increasing the CMC concentration leads to a stabilized hydrogel compared to a hydrogel prepared with a lower concentration of CMC and a longer cross-linking time.

What is claimed:

1. A method of reducing calorie intake by a subject in need thereof, comprising orally administering to the subject an effective amount of a polymer hydrogel consisting essentially of carboxymethylcellulose cross-linked with citric acid which is characterized by
   (a) a tapped density of at least 0.5 g/cm$^3$; and
   (b) a media uptake ratio in simulated gastric fluid/water (1:8) of at least about 50 at 37° C.

2. The method of claim 1 wherein the subject is obese.

3. The method of claim 1 wherein the polymer hydrogel is less than about 10% water by weight.

4. The method of claim 1 wherein at least about 95% of the polymer hydrogel by weight consists of particles in the size range of 100 pm to 1000 pm.

5. The method of claim 1 wherein the polymer hydrogel has a ratio of bonded citric acid to carboxymethylcellulose of 0.1% to 0.4% wt/wt.

6. The method of claim 1 wherein the polymer hydrogel has a ratio of bonded citric add to carboxymethylcellulose of 0.225% to 0.375% wt/wt.

7. The method of claim 1 wherein the polymer hydrogel has a degree of cross-linking from about $4\times10^{-5}$ mol/cm$^3$ to about $5\times10^{-5}$ mol/cm$^3$.

8. The method of claim 1 wherein the polymer hydrogel has a tapped density of at least 0.6 g/cm$^3$.

9. The method of claim 1 wherein the polymer hydrogel has a tapped density of about 0.6 g/cm$^3$ to about 0.8 g/cm$^3$.

10. The method of claim 1 wherein the polymer hydrogel is further characterized by an elastic modulus of at least about 350 Pa.

11. The method of claim 1 wherein the polymer hydrogel is formulated as a tablet or a capsule.

12. The method of claim 1, wherein the polymer hydrogel has a loss on drying of 10 wt % or less and is in the form of particles which are at least 80% by mass in the size range of 100 μm to 1000 μm.

13. The method of claim 12, wherein the particles are at least 95% by mass in the size range of 100 μm to 1000 μm.

14. The method of claim 12, wherein the polymer hydrogel is formulated as a capsule.

* * * * *

UNITED STATES PATENT AND TRADEMARK OFFICE
CERTIFICATE OF CORRECTION

PATENT NO. : 11,130,823 B2
APPLICATION NO. : 16/773164
DATED : September 28, 2021
INVENTOR(S) : Alessandro Sannino et al.

It is certified that error appears in the above-identified patent and that said Letters Patent is hereby corrected as shown below:

In the Claims

In Column 35
At Claim 6, Line 5, please delete the word "add" and replace with -- acid --.

Signed and Sealed this
Twenty-third Day of November, 2021

Drew Hirshfeld
*Performing the Functions and Duties of the*
*Under Secretary of Commerce for Intellectual Property and*
*Director of the United States Patent and Trademark Office*